United States Patent
DeLuca et al.

(10) Patent No.: US 7,053,075 B2
(45) Date of Patent: May 30, 2006

(54) METHODS FOR REDUCING BODY FAT USING VITAMIN D COMPOUNDS

(76) Inventors: Hector F. DeLuca, 1809 Hwy. BB, Cottage Grove, WI (US) 53531; Lori A. Plum, 6139 Hwy. N, Arena, WI (US) 53503; Hau Zhe Ke, 2 Deer La., Leydard, CT (US) 06339; Thomas A. Brown, 71 Payer La., Mystic, CT (US) 06355

( * ) Notice: Subject to any disclaimer, the term of this patent is extended or adjusted under 35 U.S.C. 154(b) by 0 days.

(21) Appl. No.: 10/996,642

(22) Filed: Nov. 24, 2004

(65) Prior Publication Data

US 2005/0143358 A1     Jun. 30, 2005

Related U.S. Application Data

(60) Provisional application No. 60/524,813, filed on Nov. 25, 2003, provisional application No. 60/524,798, filed on Nov. 25, 2003.

(51) Int. Cl.
*A61K 31/59* (2006.01)
*C07C 401/00* (2006.01)

(52) U.S. Cl. .................................. 514/167; 552/653
(58) Field of Classification Search ................ 514/167; 552/653
See application file for complete search history.

(56) References Cited

U.S. PATENT DOCUMENTS

| | | | |
|---|---|---|---|
| 5,086,191 A | 2/1992 | DeLuca et al. |
| 5,536,713 A | 7/1996 | DeLuca et al. |
| 5,585,369 A | 12/1996 | DeLuca et al. |
| 5,843,928 A | 12/1998 | DeLuca et al. |
| 6,228,393 B1 | 5/2001 | DiCosmo et al. |
| 6,310,105 B1 | 10/2001 | Damodaran |
| 6,537,981 B1 | 3/2003 | DeLuca et al. |
| 6,566,352 B1 | 5/2003 | DeLuca et al. |
| 6,579,861 B1 | 6/2003 | DeLuca et al. |

OTHER PUBLICATIONS

Wortsman et al, Decreased bioavailability of vitamin D in obesity, American Journal of Clinical Nutrition, 72:690-3, 2000.*

Arunabh et al, Body fat content and 25-hydroxyvitamin D levels in healthy women, The Journal of Clinical Endocrinology & Metabolism, 88(1):157-161, Jan. 2003.*

Kamycheva et al, Intakes of Calcium and Vitamin D Predict Body Mass Index in the Population of Northern Norway, Journal of Nutrition 132: 102-106, 2002, Copyright American Society for Nutritional Services.*

(Continued)

*Primary Examiner*—Sabiha Qazi
(74) *Attorney, Agent, or Firm*—Godfrey & Kahn, S.C.

(57) ABSTRACT

A treatment for obesity and overweight comprises administering a vitamin D analog. The analog effectively inhibits an increase in body fat to animals at risk and decreases the basal fat content of animals. The treatment has a positive effect on the lean body component such that while there is an overall decrease in body weight, there is also a decrease in percent body fat. This decrease can be proportionally greater than the overall decrease in body weight. In addition, the treatment has a positive effect on bone turnover and osteogenesis making the vitamin D analog a beneficial treatment for the symptoms of menopause. Various exemplary embodiments of the treatment use the 2-alkylidene derivatives of vitamin $D_3$, such as the 2-alkylidene-19-nor derivatives in both the R and S configurations at carbon-20.

31 Claims, 4 Drawing Sheets

Study Protocol: Effect of 2MD on OVX Rat Model
(Restoration Mode)

OTHER PUBLICATIONS

Mark A. Moyad, Urologic Nursing, Feb. 2003, vol. 23, No. 1, 69-74.*

Activation of Methylenetriphenylphosphorane by Reaction with t-Butyl-or sec—Butyllithium, Tetrahedron Letters, vol. 26, No. 5, pp 555-558, Corey et al.

Calciferol and its Relatives. Part 22.[1] A Direct Total Synthesis of Vitamin $D_2$ and Vitamin $D_3$[2], Journal of the Chemical Society Perkin Transactions 1, pp 590-595, Lythgoe et al.

Novel Synthesis of 19-Nor-Vitamin D Compounds, Tetrahedron Letters, vol. 32, No. 52, pp 7663-7666, Perlman et al.

1a, 25-Dihydroxy-19-Nor-Vitamin $D_3$, A Novel Vitamin D-Related Compound with Potential Therapeutic Activity, Tetrahedron Letters, vol. 31, No. 13, pp 1823-1824, Perlman et al.

The ovariectomized rat model of postmenopausal bone loss, Bone and Mineral, vol. 15, No. 3, pp 175-192, Kalu et al.

A potent analog of 1, 25-dihydroxyvitamin $D_3$ selectivly induces bone formation, PNAS, vol. 99, No. 21, pp 13487-13491, Shevde et al.

2-Methylene-19-nor-(20S)-1,25-dihydroxyvitamin $D_3$ Potently Stimulates Gene-specific DNA Binding of the Vitamin D Receptor in Osteoblasts, Journal of Biological Chemistry, vol. 278, No. 34, pp 31756-31765, Yamamoto et al.

24-and 26-homo-1,25-dihydroxyvitamin $D_3$: Preferential activity in inducing differentiation of human leukemia cells HL-60 in vitro, Proc. Natl. Acad. Sci. USA, May 1987, vol. 84, pp 2610-2614, Ostrem et al.

Skeletal response of ovariectomized rats to low and high doses of 17β-estradiol, Bone and Mineral, vol. 14, No. 3, (1991), pp 175-187, Kalu et al.

Stereocontrolled Total Synthesis of 1,25-Dihydroxycholecalciferol[1] and 1,25-Dihydroxyergocalciferol, J. Org. Chem, vol. 51, No. 16, (1986) pp 3098-3108, Baggiolini et al.

Studies on a Convergent Route to Side-Chain Analouges of Vitamin D: 25-Hydroxy-23-oxavitamin $D_2$[1], J. Org. Chem., vol. 48, No. 9, (1983), pp 1414-1417, Toh et al.

Studies on the Synthesis of Side-Chain Hydroxylated Metabolites of Vitamin $D_3$. Synthesis of 25-Ketovitamin Dand 25-Hydroxyvitamin $D_3$[1], J. Org. Chem., vol. 51, No. 8, (1986), pp 1269-1272, Mascareñas et al.

Synthesis and Biological Activity of 2-Hydroxy and Alkoxy Analogs of 1a, 25-Dihydroxy-19-norvitamin $D_3$, J. Org. Chem., vol. 37, No., 22,(1994), pp 3730-3738, Sicinski et al.

Synthetic Approaches to Vitamin D and its Relatives, Chemical Society Reviews, vol. 9, (1980), pp 449-475, Lythgoe et al.

The Wittig Reaction Using Methylsulfinyl Carbonion-Dimethyl Sulfoxide[1], Dept. of Chemistry, Harvard University, Cambridge 38, Massachusetts, vol. 28, (1962), pp 1128-1129, Greenwald et al.

* cited by examiner

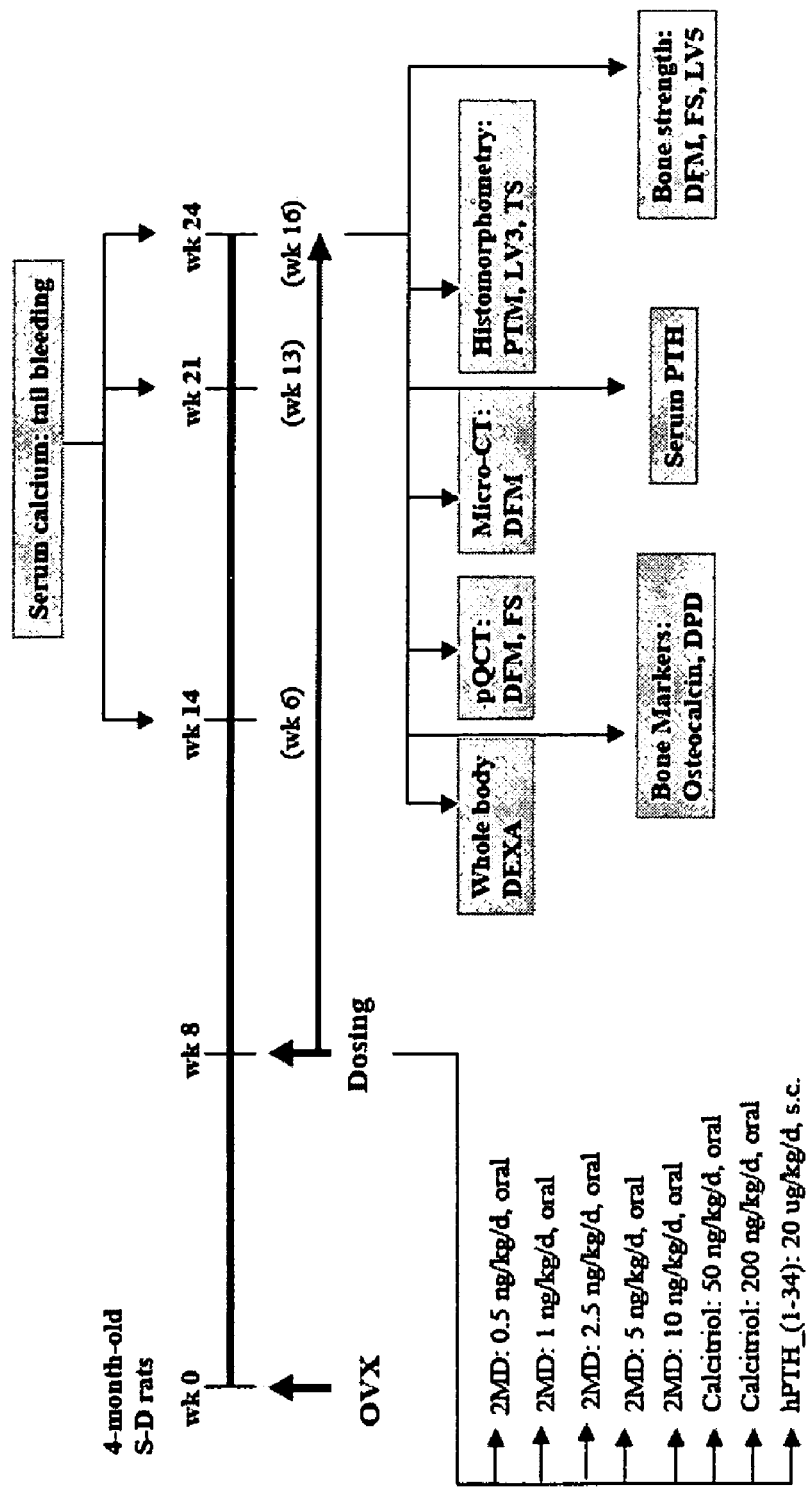

Fig. 2

| | |
|---|---|
| Animals: | S-D female rats (TACONIC, German Town, NY) arrived on 09/19/02 |
| Surgery: | Sham (n = 20) or OVX (n = 90) at 4 months of age. |
| Diet: | AIN-76A Rodent Diet (Research Diet Inc., New Brunswick, NJ; 0.5% Ca/0.4% P) |

Dosing and Vehicles (total 16 weeks)
Beginning 8 weeks post-surgery for 16 weeks.
2MD: 10, 5, 2.5, 1, 0.5 ng/kg/day, in 100 ul of vegetable oil per rat, deliver to the back of the tongue.
Calcitriol: 50 & 200 ng/kg/day, in 100 ul of vegetable oil per rat, deliver to the back of the tongue.
Sham+Veh: 100 ul of vegetable oil per rat, deliver to the back of the tongue.
OVX+Veh: 100 ul of vegetable oil per rat, deliver to the back of the tongue.

| Groups | Dose | -0 wks | 8 wk | 24 wks |
|---|---|---|---|---|
| SHAM+Veh | Vehicle, p.o. | SHAM | 10 | 10 |
| OVX+Veh | Vehicle, p.o. | OVX | 9 | 9 |
| OVX + 2MD | 10 ng/kg/d, p.o. | OVX | | 9 |
| OVX + 2MD | 5 ng/kg/d, p.o. | OVX | | 9 |
| OVX + 2MD | 2.5 ng/kg/d, p.o. | OVX | | 9 |
| OVX + 2MD | 1 ng/kg/d, p.o. | OVX | | 9 |
| OVX + 2MD | 0.5 ng/kg/d, p.o. | OVX | | 9 |
| OVX + Calcitriol | 50 ng/kg/d, p.o. | OVX | | 9 |
| OVX + Calcitriol | 200 ng/kg/d, p.o. | OVX | | 9 |
| OVX + hPTH | 20 µg/kg/d, s.c. | OVX | | 9 |

Endpoints:
Body weight at Baseline and autopsy;
Muscle weight; Levitor ani, Soleus, Gastrocemius
Serum bone markers: osteocalcin, PYD,
Serum PTH
Serum calcium, phosphorus: 2 hours and 24 hours after last dosing (tail bleeding)
Right Femur: pQCT, Micro-CT
Right Tibial: histomorphometry
LV1-3: save for histomorphometry
Left femur and LV4-6: bone strength
Whole body DEXA at 16 weeks

METHODS FOR REDUCING BODY FAT USING VITAMIN D COMPOUNDS

PRIORITY

Priority is hereby claimed to provisional applications Ser. Nos. 60/524,813 and 60/524,798, each filed Nov. 25, 2003, each of which is incorporated herein by reference in its entirety.

FIELD OF THE INVENTION

This invention is generally directed to a method of using one or more vitamin D analogs to reduce body fat of an animal.

BACKGROUND OF THE INVENTION

Obesity and overweight have reached world-wide epidemic proportions. Further, overweight and obesity are highly correlated with the incidence of high blood pressure and high cholesterol. The United Nations has identified three of the world's top ten health risks as obesity, high blood pressure and high cholesterol. Globally, there are more than one billion overweight adults and at least 300 million of these overweight adults are considered obese. In the United States alone, over 60% of the population is considered overweight or obese. In addition, overweight is one of the fastest growing disorders among children. The incidence of childhood overweight is approaching levels of one in three, resulting in over 22 million children under age 5 being overweight in Europe and North America alone.

Besides being recognized as a disease in its own right, obesity is also associated with such life-threatening diseases as high blood pressure, diabetes, coronary artery disease, congestive heart failure, stroke, osteoarthritis, various cancers and reproductive health and psychological disorders. In 1998, the United States alone had economic losses of over $92 billion due to overweight and obesity. Further, there is no doubt that obesity increases mortality because of its pathophysiologic effects.

Overweight and/or obesity can be empirically determined by calculation of either the Body Mass Index (BMI) or the lean body mass. The BMI is the product of the weight (in kilograms) of an individual divided by the height (in meters) squared. For adults, a BMI of 25 or more is considered overweight and a BMI of 30 or more is considered obese. Lean body weight is the total body weight minus the weight of the adipose or fat component. Typically, men are considered overweight when they have a fat content of about 24 percent or more and women 30 percent or more. Lean body weight, therefore represents the sum of a persons bones, muscles and organs. Lean body weight can be calculated using empirical formulas and objectively using dual-energy X-ray absorptiometry (DEXA). DEXA determines the body weight contribution of the lean soft tissue, fat soft tissue and bone compartments by differentiating between the tissue attenuation of two different X-ray wave lengths.

The major factor responsible for the increase in overweight and obesity appears to be environmental or cultural rather than hereditary. However, adopted children tend to have weight problems more like their biological parents than their adoptive parents, indicating that genetics plays at least a minor role. Obesity and overweight tends to run in families, most likely resulting from shared lifestyle and eating habits. Children of obese or overweight parents have a 25 to 30% chance of becoming obese themselves. However, the current epidemic of overweight and obesity is ample evidence that genetics may actually be reinforcing an environmental problem. Thus, family background, whether environmental or genetic, is predictive of a tendency or risk of becoming overweight or obese.

Critical life periods also are correlated to weight gain. For men, the critical periods are between 35 and 40 years, after marriage and after retirement. For women the critical periods occur during adolescence, after marriage, during pregnancy, during menopause and after retirement. In women, the problem of weight gain is further exacerbated by the fact that women tend to have less lean body mass. Lean body mass is more metabolically active than fat soft tissue. Consequently, women have less ability to burn excess calories than men. Generally, men have higher rates of overweight while women have higher rates of obesity.

In women, the effects of overweight or obesity may have even more serious health consequences during menopause. For example, women approaching menopause are at an increased risk of heart disease and osteoporosis, weight gain and urinary incontinence. During menopause, if a woman is more than 30% overweight, she is at an increased risk of heart disease. The risk of heart disease and urinary incontinence can be reduced by decreasing body fat while the risk of osteoporosis can be treated by a variety of methods, including hormone replacement therapy (HRT), bisphosphonates and selective estrogen receptor modulators (SERMs). Pharmacologic treatments directed to preventing or ameliorating osteoporosis may have serious side effects, including cardiovascular disease, increased blood pressure and an increased risk of breast cancer, and do not address the tendency for weight gain and its associated risks.

There are a wide variety of techniques and methods advocated to treat obesity and overweight. Current weight control methods range from surgical intervention, to diet modification, to acute reductions in caloric intake, to pharmacologic or naturopathic remedies, both of which are designed to increase metabolism and/or suppress the appetite. Each of these methods has its deficiencies. For example, surgical methods to reduce the intake of food include stapling the stomach or reducing the length of the small intestine. While such surgical methods are generally effective, they are limited to the morbidly obese because of the risk of serious and/or fatal complications.

A more obvious approach to weight loss is altering dietary habits. While it is generally conceded that weight loss will result from consuming less calories than expended, such methods do not appear to be a viable solution for the legions of overweight. Therefore, a large number of special diets are advocated to facilitate weight loss. For example, some individuals use diets that focus on shifting calories between food groups, such as high protein/low carbohydrate diets or grapefruit diets. Some individuals resort to fad or crash diets or acute reductions in food consumption. Unfortunately, the rapid decrease in body weight without adequate nutritional intake may have a boomerang effect resulting in increased obesity, as well as physiologic repercussions, such as acidosis or ketosis, that occasionally results in death or other serious complications. Further, while a variety of appetite suppressants are espoused, many of them do not work and some may be fatal. For example, phen-fen, a combination of fenfluramine and phentermine, was found to cause fatal heart valve damage only after it had become a widely used dietary supplement.

Methods of decreasing overweight or obesity that focus on rapidly decreasing caloric intake may also be counterproductive. While decreased food intake is an effective method of losing weight, the energy stored in fat cells is generally the last energy store utilized by the body. Generally, the first energy stores liberated result in glucose metabolism and the second result in protein metabolism. Because glucose stores are relatively small, the result of a restricted diet without enough exercise to maintain muscle mass is the mobilization of energy stored in the protein compartment. Because lean body mass has a much higher metabolic rate than does adipose tissue, and because adipose tissue is initially spared during times of fast, diets that restrict caloric intake often result in a decrease in lean body mass before any energy derived from the fat compartment is utilized. Thus, the abrupt decrease in caloric intake may have the ironic effect of lowering lean body mass, lowering total metabolic rate and decreasing the mobilization of fat stores. The result is that while a decrease in total body weight may be achieved, the weight reduction comes at the expense of the lean body component rather than the fat component, effectively increasing the individual's percent body fat.

SUMMARY OF THE INVENTION

While there are an abundance of methods that attempt to control weight gain or decrease body fat, statistics show that a growing number of individuals are becoming overweight and/or obese. Methods such as diet modification, appetite suppression, diets and pharmacologic and/or surgical intervention are not adequate to prevent the growing epidemic of overweight and obesity. In addition, overweight and its attendant health risks, heart disease and high cholesterol, are recognized symptoms of menopause affecting previously healthy-weight women at the same time that they become at risk for osteoporosis. Significantly, even if women entering menopause were previously successful with conventional methods of maintaining a healthy weight and lean body mass, such women would still be at an increased risk for weight gain, cardiovascular disease, osteoporosis and other health risks associated with menopause.

This invention provides a method for reducing total body fat in an animal.

This invention separately provides a method of reducing the body fat component of an animal without reducing lean body mass.

This invention separately provides a method for reducing body fat component of an animal without resorting to diets or surgical intervention.

This invention separately provides a method for reducing body fat component of an animal while inducing an increase in bone mass or osteogenesis.

This invention separately provides a method for inhibiting an increase in the body fat component of an animal.

This invention separately provides a method for inhibiting an increase in the body fat component of an animal without reducing the lean body mass of the animal.

This invention separately provides a method of inhibiting an increase in the total body fat of an animal while inducing an increase in bone mass or osteogenesis.

This invention separately provides a method of treating obesity in an animal.

This invention separately provides a method of treating obesity in an animal by decreasing the percent body fat of the animal.

This invention separately provides methods of treating obesity in an animal by decreasing the body fat component of the animal while maintaining lean body mass.

This invention separately provides a method of treating obesity in an animal by decreasing the body fat component of the animal while maintaining lean body mass and encouraging bone mineralization and osteogenesis.

This invention separately provides a systems and methods for alleviating symptoms of menopause by controlling weight gain and its accompanying cardiovascular risks while concomitantly having a beneficial effect on bone metabolism and osteogenesis.

This invention provides a method of reducing the percent body fat of an animal by administering an effective amount of a 2-alkylidene-vitamin $D_3$ derivative to an overweight and/or obese animal.

In various exemplary embodiments, methods for inhibiting an increase in the fat component of an animal according to this invention include administering an effective amount of a 2-alkylidenevitamin $D_3$ derivative. In various exemplary embodiments, the 2-alkylidene vitamin $D_3$ derivative is a 2-alkylidene-19-nor vitamin $D_3$ derivative. In various exemplary embodiments, the 2-alkylidene-19-nor-vitamin $D_3$ derivatives include analogs in which the chiral center at carbon-20 has either an R or S configuration or is a racemic mixture of the R and S configurations. In various exemplary embodiments, the 2-alkylidene-19-nor vitamin $D_3$ derivative is 2-methylene-19-nor vitamin $D_3$. In various exemplary embodiments, the 2-alkylidene-19-nor-vitamin $D_3$ derivative is 2-methylene-19-nor-(20S)-1α,25 dihydroxyvitamin $D_3$ (2MD).

In various exemplary embodiments, methods for reducing the fat component of an animal include administering an effective amount of a 2-alkylidene vitamin $D_3$ derivative. In various exemplary embodiments, the 2-alkylidene vitamin $D_3$ derivative is a 2-alkylidene-19-nor vitamin $D_3$ derivative. In various exemplary embodiments, the 2-alkylidene-19-nor-vitamin $D_3$ derivatives include analogs in which the chiral center at carbon-20 has either an R or S configuration or is a racemic mixture of the R and S configurations. In various exemplary embodiments, the 2-alkylidene-19-nor vitamin $D_3$ derivative is 2-methylene-19-nor vitamin $D_3$. In various exemplary embodiments, the 2-alkylidene-19-nor-vitamin $D_3$ derivative is 2-methylene-19-nor-(20S)-1α,25 dihydroxyvitamin $D_3$ (2MD).

In various exemplary embodiments, methods for reducing the percent body fat of an animal according to this invention include administering an effective amount of a 2-alkylidene vitamin $D_3$ derivative. In various exemplary embodiments, the 2-alkylidene vitamin $D_3$ derivative is a 2-alkylidene-19-nor vitamin $D_3$ derivative. In various exemplary embodiments, for the 2-alkylidene-19-nor-vitamin $D_3$ derivatives include analogs in which the chiral center at carbon-20 has either an R or S configuration or is a racemic mixture of the R and S configurations. In various exemplary embodiments, the 2-alkylidene-19-nor vitamin $D_3$ derivative is 2-methylene-19-nor vitamin $D_3$. In various exemplary embodiments, the 2-alkylidene-19-nor-vitamin $D_3$ derivative is 2-methylene-19-nor-(20S)-1α,25 dihydroxyvitamin $D_3$ (2MD).

In various exemplary embodiments, methods for reducing the percent body fat of an animal while encouraging osteogenesis according to this invention include administering an effective amount of a 2-alkylidene vitamin $D_3$ derivative. In various exemplary embodiments, the 2-alkylidene vitamin $D_3$ derivative is a 2-alkylidene-19-nor vitamin $D_3$ derivative. In various exemplary embodiments, the 2-alkylidene-19-nor-vitamin $D_3$ derivatives include analogs in which the chiral center at carbon-20 has either an R or S configuration or is a racemic mixture of the R and S configurations. In various exemplary embodiments, the 2-alkylidene-19-nor vitamin $D_3$ derivative is 2-methylene-19-nor vitamin $D_3$. In various exemplary embodiments, the 2-alkylidene-19-nor-vitamin $D_3$ derivative is 2-methylene-19-nor-(20S)-1α,25 dihydroxyvitamin $D_3$ (2MD).

In various exemplary embodiments, methods for prophylactically treating individuals at risk of becoming overweight or obese according to this invention include administering an effective amount of a 2-alkylidene vitamin $D_3$ derivative. In various exemplary embodiments, the 2-alkylidene vitamin $D_3$ derivative is a 2-alkylidene-19-nor vitamin $D_3$ derivative. In various exemplary embodiments, the 2-alkylidene-19-nor-vitamin $D_3$ derivatives include analogs in which the chiral center at carbon-20 has either an R or S configuration or is a racemic mixture of the R and S configurations. In various exemplary embodiments, the 2-alkylidene-19-nor vitamin $D_3$ derivative is 2-methylene-19-nor vitamin $D_3$. In various exemplary embodiments, the 2-alkylidene-19-nor-vitamin $D_3$ derivative is 2-methylene-19-nor-(20S)-1α,25 dihydroxyvitamin $D_3$ (2MD).

In various exemplary embodiments, methods for alleviating the symptoms of menopause in an animal according to this invention include administering an effective amount of a 2-alkylidene vitamin $D_3$ derivative. In various exemplary embodiments, the 2-alkylidene vitamin $D_3$ derivative is a 2-alkylidene-19-nor vitamin $D_3$ derivative. In various exemplary embodiments, the 2-alkylidene-19-nor-vitamin $D_3$ derivatives include analogs in which the chiral center at carbon-20 has either an R or S configuration or is a racemic mixture of the R and S configurations. In various exemplary embodiments, the 2-alkylidene-19-nor vitamin $D_3$ derivative is 2-methylene-19-nor vitamin $D_3$. In various exemplary embodiments, the 2-alkylidene-19-nor-vitamin $D_3$ derivative is 2-methylene-19-nor-(20S)-1α,25 dihydroxyvitamin $D_3$ (2MD).

The vitamin $D_3$ derivatives according to this invention can be administered in any effective dose. In various exemplary embodiments, the vitamin $D_3$ derivatives are administered in ranges of from about 0.001 μg per day to 100 mg per day. In various other exemplary embodiments, the vitamin $D_3$ derivatives are administered in ranges of about 0.010 μg per day to 1,000 μg per day.

The vitamin $D_3$ derivatives according to this invention can be administered in any effective known or later developed manner. In various exemplary embodiments, the vitamin $D_3$ derivatives are administered rectally, topically, transdermally, or by injection, inhalation, therapeutic implant or the like.

These and other features and advantages of various exemplary embodiments of the methods according to this invention are described in, or are apparent from, the following detailed description of various exemplary embodiments of the methods according to this invention.

BRIEF DESCRIPTION OF THE FIGURES

Various exemplary embodiments of the methods of this invention will be described in detail, with reference to the following figures, wherein:

FIG. 1 is a flow-chart illustrating one exemplary study protocol and showing the experimental groups, their surgical treatments and dosing regime with the measurements taken during the investigation;

FIG. 2 is a table further delineating the treatment groups illustrated in FIG. 1;

DETAILED DESCRIPTION OF THE EXEMPLARY EMBODIMENTS

Figure 3:
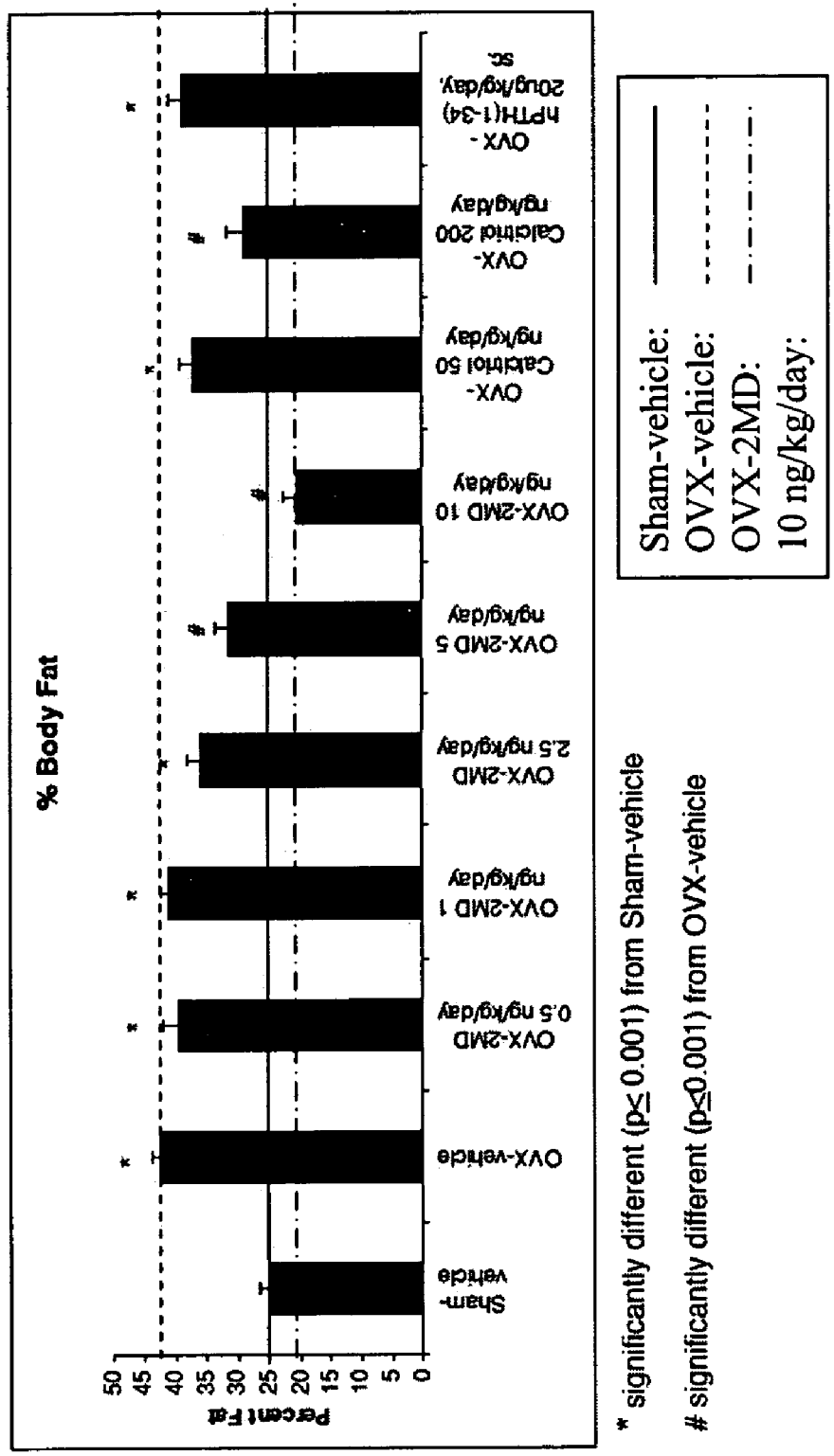
FIG. 3 is a histogram showing the effect on percent body fat of providing a specific 2-alklyidene-19-nor-vitamin $D_3$ derivative, 2MD, to a test animal, compared to sham-vehicle and ovariectomized-vehicle controls as measured by DEXA.

A natural hormone, as both 1α,25-dihydroxyvitamin $D_3$ (calcitriol) and its analog in ergosterol series, i.e., 1α,25-dihydroxyvitamin $D_2$, is known to be a highly potent regulator of calcium homeostasis in animals, including humans. More recently, Ostrem et al, Proc. Natl. Acad. Sci. USA, 84, 2610 (1987), established these compounds are active in cellular differentiation. Many structural analogs of these metabolites have been prepared and tested, including 1α-hydroxyvitamin $D_3$, 1α-hydroxyvitamin $D_2$ and various side chain homologated vitamins and fluorinated analogs. Some of these compounds exhibit an interesting separation of activities in cell differentiation and calcium regulation. This difference in activity may be useful in the treatment of a variety of diseases, such as, for example, renal osteodystrophy, vitamin D-resistant rickets, osteoporosis, psoriasis, and certain malignancies.

Recently, a new class of vitamin D analogs has been discovered. This class is the so called 19-nor-vitamin D compounds. The 19-nor-vitamin D compounds are characterized by replacing the exocyclic A-ring methylene group (carbon 19), which is typical of the vitamin D system, with two hydrogen atoms. Biological testing of such 19-nor-analogs, such as, for example, 1α,25-dihydroxy-19-nor-vitamin $D_3$, has revealed a selective activity profile with high potency in inducing cellular differentiation, with very low calcium mobilizing activity. Thus, these compounds are potentially useful as therapeutic agents for treating malignancies or treating various skin disorders. Two different methods of synthesizing such 19-nor-vitamin D analogs are described in Perlman et al, Tetrahedron Letters 31, 1823 (1990); Perlman et al, Tetrahedron Letters 32, 7663 (1991); and U.S. Pat. No. 5,086,191, each incorporated herein by reference in its entirety.

In a continuing effort to explore the 19-nor class of pharmacologically important vitamin D compounds, the inventors have now synthesized and are testing certain analogs which are characterized by transpositioning the A-ring exocyclic methylene group from carbon 10 (C-10) to carbon 2 (C-2), creating the so-called 2-alkylidene-19-nor-vitamin D compounds. Such vitamin D analogs are interesting targets because the relatively small exomethylene unit at C-2 should not interfere with vitamin D receptors. On the other hand, molecular mechanics studies performed on the 2-methylene-19-nor-vitamin D compounds showed that a change in the A-ring conformation can be expected to result in the "flattening" of the cyclohexanediol ring. Moreover, introducing the 2-methylene group into the 19-nor-vitamin D carbon skeleton changes the character of its (1α- and 3β) A-ring hydroxyls, such that they are both changed to the allylic position, which is crucial for the biologic activity in the 1α-hydroxyl group of the natural 1α,25-(OH)$_2$D$_3$ hormone molecule.

The inventors' current investigations into the pharmacologic activity of the 2-alkylidene-19-nor-vitamin $D_3$ derivatives include their effect on classical vitamin D targets, such as calcium metabolism and bone formation. Some of the 2-alkylidene-19-nor-vitamin $D_3$ derivatives being studied include: 1α-hydroxy-2-methylene-19-nor-pregnacalciferol (2-Mpregna), (20S)-1α-hydroxy-2-methylene-19-nor-bishomopregnacalciferol (2-MbisP) and 1α-hydroxy-2-methylene-19-nor-homopregnacalciferol (2MP), all described in U.S. Pat. No. 6,566,352, which is incorporated herein by reference in its entirety. During the course of these investigations, another 2-alkylidene-19-nor-vitamin D compound, 2-methylene-19-nor-(20S)-1α,25 dihydroxyvitamin $D_3$ (2MD) was synthesized and studied. Investigations into the calcium regulatory activity of 2MD in the classical vitamin $D_3$ pathway showed that 2MD is a potent regulator of osteogenesis.

Unexpectedly, 2MD was also found to have a profound effect on adipose tissue. Specifically, experimental animals given 2MD were found to have a significant inhibition in weight gain and decrease in body fat composition. Various exemplary embodiments of methods according to this invention include using a vitamin D analog to reduce body fat and/or to inhibit the accumulation of body fat. In various exemplary embodiments, the vitamin D analog is a 2-alkylidene-19-nor-vitamin $D_3$ derivative, where, in various exemplary embodiments, the chiral center at carbon-20 is in either the R or the S configuration. In various exemplary embodiments, the 2-alkylidene-19-nor-vitamin $D_3$ derivative is 2-methylene-19-nor-(20S)-1α,25 dihydroxyvitamin $D_3$ (2MD).

The synthesis of 2-alkylidene-19-nor vitamin $D_3$ derivatives in both their R and S conformations has previously been described in U.S. Pat. Nos. 5,086,191; 5,536,713; 5,585,369; 5,843,928; 6,537,981, 6,579,861, each incorporated herein by reference in its entirety. The inventors are conducting an on-going investigation on the 19-nor analogs, in both R and S conformations, for their effect on calcium and bone metabolism. However, during the course of the investigations, the inventors have surprisingly found that ovariectomized rats administered 2MD experienced a significant fat loss without any loss of muscle mass.

Generally, the 2-alkylidene-19-nor vitamin $D_3$ derivatives can be represented by the formula I:

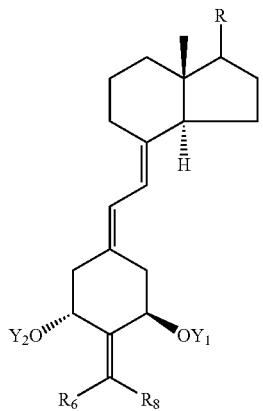

I where $Y_1$ and $Y_2$, which may be the same or different, are each selected from the group consisting of hydrogen and a hydroxy-protecting group; $R_6$ and $R_8$, which may be the same or different, are each selected from the group consisting of hydrogen, alkyl, hydroxyalkyl and fluoroalkyl, or, when taken together represent the group —$(CH_2)_x$— where X is an integer from 1 to 5; and where the group R represents any of the typical side chains known for vitamin D-type compounds. It should be appreciated that R encompasses any later-discovered side chain usable for vitamin D-type compounds, except for particular later-discovered side chains that significantly interfere with the functioning of the 2-alkylidene 19-nor vitamin $D_3$ derivatives. A representative set of such vitamin D-type compound is set forth below.

In various exemplary embodiments, R can represent a saturated or unsaturated hydrocarbon radical of 1 to 35 carbons. This hydrocarbon radical may be straight-chain, branched or cyclic and may contain one or more additional substituents. These substituents include, for example, hydroxy- or protected-hydroxy groups, fluoro, carbonyl, ester, epoxy, amino or other heteroatomic groups. Various exemplary side chains of this type are represented by the structure below, where the stereochemical center (corresponding to C-20 in steroid numbering) has the R or S configuration (i.e. naturally or non-naturally occurring configuration about carbon 20). In various exemplary embodiments, R is selected from the group of Y, —OY, —$CH_2$ OY, C/CY and —CH=CHY, where the double bond may have the cis or trans geometry.

In these compounds, Y is selected from the group of hydrogen, methyl, —$COR^5$ and a radical of the structure:

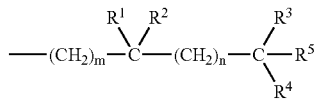

where m and n independently represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched and, optionally, bear a hydroxy or protected-hydroxy substituent, and where $R^1$ and $R^2$, taken together, represent an oxo group, or an alkylidene group, =$CR^2 R^3$, or the group —$(CH_2)_p$—, where p is an integer from 2 to 5, and where $R^3$ and $R^4$, taken together, represent an oxo group, or the group —$(CH_2)_q$—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —$CH(CH_3)$—, —$CH(R^3)$—, or —$CH(R^2)$— at positions 20, 22, and 23, respectively, may be replaced by an oxygen or sulfur atom.

As used herein, the term "hydroxy-protecting group" encompasses and signifies any group usable to at least temporarily protect hydroxy functions, and includes for example, alkoxycarbonyl, acyl, alkylsilyl or alkylarylsilyl groups (hereinafter referred to simply as "silyl" groups), and alkoxyalkyl groups. Alkoxycarbonyl protecting groups include alkyl-O—CO— groupings, such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The term "alkyl" as used herein, denotes a straight-chain or branched alkyl radical of 1 to 10 carbons, in all its isomeric forms. Alkoxyalkyl protecting groups include groupings such as methoxymethyl, ethoxymethyl, methoxyethoxymethyl, or tetrahydrofuranyl and tetrahydropyranyl. Various exemplary silyl-protecting groups include trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any such groups usable to temporarily or permanently protect hydroxy functions, such as, for example, the silyl, alkoxyalkyl, acyl or alkoxycarbonyl groups discussed above. The terms "hydroxyalkyl", "deuteroalkyl" and "fluoroalkyl" encompasses an alkyl radical substituted by one or more hydroxy, deuterium or fluoro groups, respectively.

Various exemplary embodiments of side chains that include R, occurring with the 2-alkylidene-analogs, are structures having the R configuration at the chiral center at carbon-20 and represented by formulas (a), (b), (c), (d) and (e) below, such as, for example, the side chain as it occurs in 25-hydroxyvitamin $D_3$ (a); vitamin $D_3$ (b); 25-hydroxyvitamin $D_2$ (c); vitamin $D_2$ (d); and the C-24 epimer of 25-hydroxyvitamin $D_2$ (e). Formulas (f)–(j) represent the 20S isomers of formulas (a)–(e). In formulas (a)–(j), the wavy line to the methyl group at C-20 represents that carbon 20 may be in either the R or S configuration:

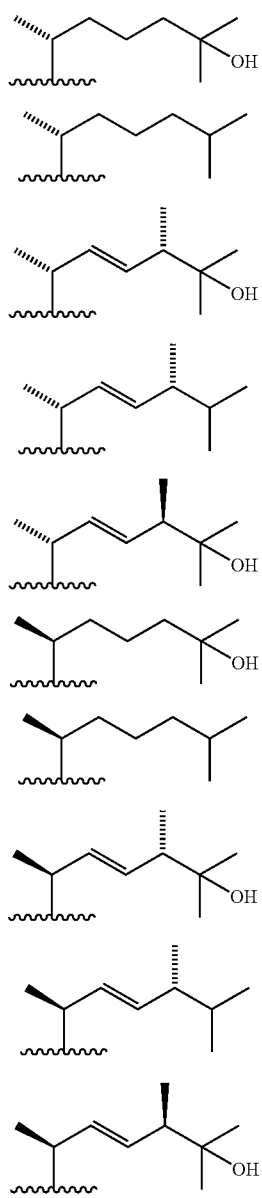

One important characteristic of the 19-nor analogs of vitamin D is that they have a potent effect on cell differentiation. As described in the incorporated 713, the 19-nor vitamin D analogs promote the differentiation of human leukemia cells to non-malignant monocytes at concentrations similar to that of native vitamin $D_3$. In addition, the 19-nor-(20R) compounds described in the incorporated 713 patent have biological activity in intestinal transport similar to that of 1,25-$(OH)_2D_3$. However, those particular 19-nor-(20R) compounds possess little or no bone calcium mobilizing activity.

Recently, the inventors investigated the 19-nor-(20S) vitamin $D_3$ analogs for their effects on calcium regulation and bone mineralization. Previously, Kalu, D. N. Bone Miner. 15, 175 (1991), showed that ovariectomized rats provide a suitable model that mimics the effects of menopause in human women. Shevde et al. Proc. Natl. Acad. Sci. 99, 13487 (2002), incorporated herein by reference in its entirety, showed that the 2-methylene-19-nor-(20S)-1α,25-dihydroxyvitamin $D_3$ analog has particular promise in inducing osteogenesis in ovariectomized rats. Inducing osteogenesis is usable as a treatment of osteoporosis. In the studies described in Shevde et al., the 2-alkylidene-19-nor-(20S)-1α,25-dihydroxyvitamin $D_3$ derivative, 2MD, was found to have a low intestinal calcium transport activity and a high bone calcium mobilization activity. Analysis of the bone mobilizing effects of 2MD indicates that 2MD causes both bone resorption and bone formation. In various exemplary embodiments, this results in an increase in bone mineral density. Because bone resorption is a necessary component of osteogenesis or bone synthesis and growth, this study indicates that 2MD increases new bone growth and that the increase in bone formation outweighs the decrease in bone mass due to bone resorption. These findings were confirmed and extended by Yamamoto et al., J. Biol. Chem. 278, 31756 (2003), which shows that osteoclast formation increased osteoblast activity and that 2MD was at least 100-fold more active than calcitriol in inducing genes in the osteoblast cell line while concomitantly suppressing osteoprotegerin, which acts to increase bone resorption.

The inventors designed investigations further exploring the pathways by which 2MD exerts its osteogenic effects. FIGS. 1 and 2 illustrate the experimental design of these investigations into the calcium regulatory and osteogenic effects of 2MD, calcitriol and parathyroid hormone (PTH). In these experiments, DEXA analysis was used to monitor the change in body composition of the treatment groups.

FIG. 3 is a histogram representing the change in percent body fat of the various treatment groups. The basal percent body fat of the sham-vehicle controls with respect to the other treatment groups is represented by the solid line, the percent body fat of the ovariectomized (OVX)-controls with respect to the other treatment groups is shown by the dashed line, while percent body fat of the OVX-2MD 10 ng/kg/day group with respect to the other treatment groups is represented by the chained line. FIG. 3 confirms a significant increase in percent body fat of ovariectomized rats, as expected. Surprisingly, the ovariectomized animals given 2MD at the 5 and 10 ng/kg/day dose had a significantly less increase in percent body fat than did the ovariectomized-vehicle controls. In addition, there was a noticeable trend for a reduced increase in percent body fat for animals administered 2MD at doses as low as 0.5 ng/kg/day. Further, the animals given 2MD at doses of 10 ng/kg/day not only had significantly less percent body fat than did the ovariectomized controls, but also had noticeably less percent body fat than did the sham-operated controls. Thus, FIG. 3 illustrates that not only does 2MD protect rats undergoing ovariectomy from gaining an increase in percent body fat, but that, when compared to the basal level of the sham-operated controls, rats given 2MD actually had a decrease in basal percent body fat. This result illustrates that 2MD not only inhibits an increase in body fat following ovariectomy but also decreases the body fat component from the basal level represented by the sham-operated controls.

In various exemplary embodiments of methods according to this invention, the 2-alkylidene-19-nor-1α,25-dihydroxyvitamin $D_3$ analogs are particularly useful in inhibiting an increase in the percent body fat in animals. Further, in various other exemplary embodiments of methods according to the invention, administering an effective amount of a 2-alkylidene-19-nor-1α,25-dihydroxyvitamin $D_3$ analog tends to decrease the percent body fat of the animal administered the compound. In various exemplary embodiments, the 2-methylene-19-nor-1α,25-dihydroxyvitamin $D_3$ analog, in either the R or S configuration, is used as the administered compound to reduce percent body fat. In various exemplary embodiments, 2-methylene-19-nor-(20S)-1α,25-dihydroxyvitamin $D_3$ analog (2MD) is used as the administered compound to reduce percent body fat. In still other exemplary embodiments, a racemic mixture of the 20S and the 20R conformations is used as the administered compound to reduce percent body fat.

Figure 4:
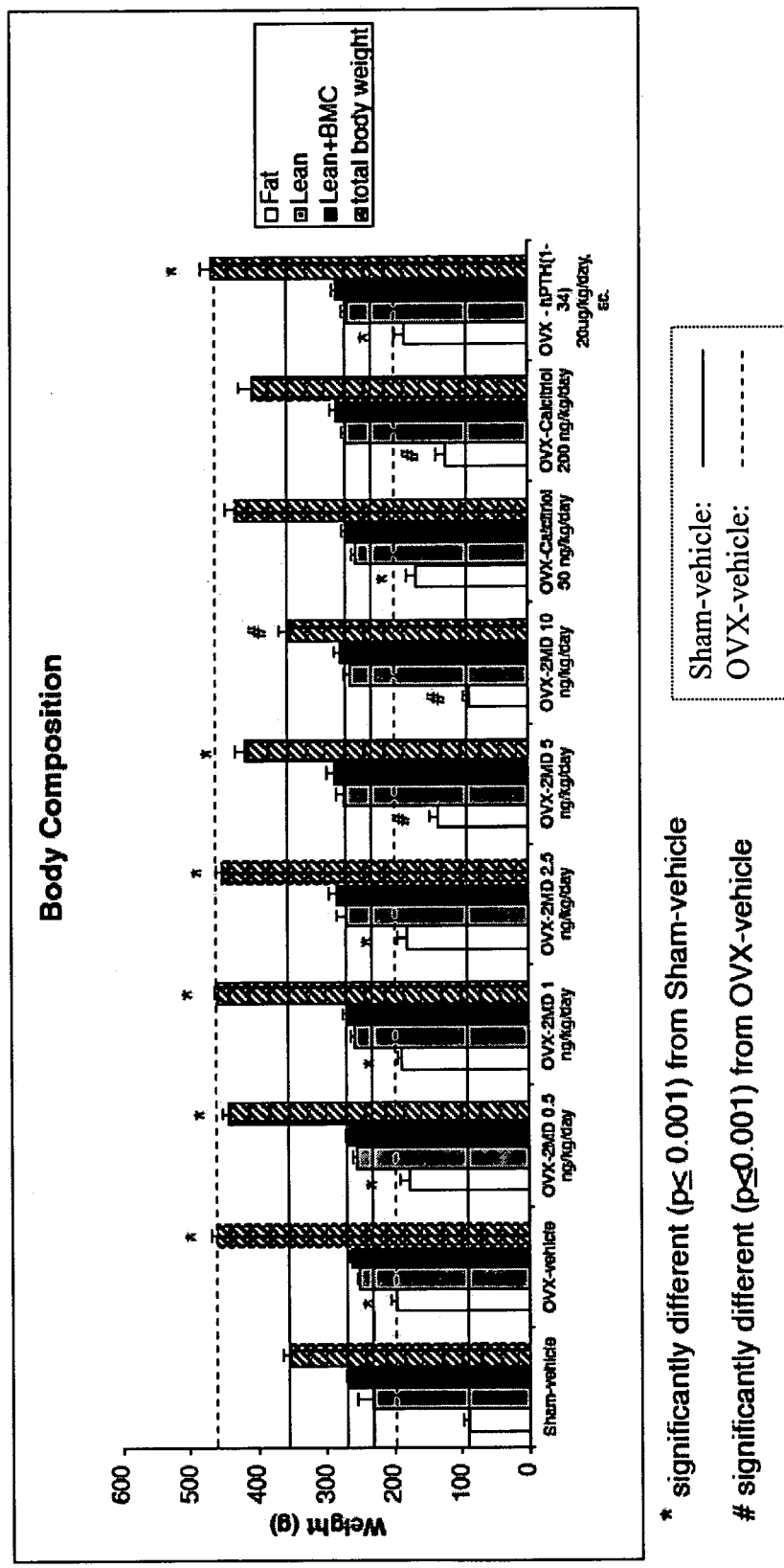
FIG. 4 is a histogram showing the results of providing 2MD on body composition in ovariectomized rats as measured by DEXA.

FIG. 4 is a histogram of the weight contributions of the individual body compartments as measured by DEXA. The solid lines represent the basal level of the individual compartments with respect to the other treatment groups, while the dashed lines represent the values of the body compartments for the ovariectomized-vehicle group with respect to the other groups. FIG. 4 shows the results of the DEXA analysis when used to investigate the individual contributions of the fat, lean and bone mineral components of the total body weight. FIG. 4 confirms the results shown in FIG. 3. When each body component is analyzed individually, the animals given 2 MD at 5 and 10 ng/kg/day had significantly less body fat than the ovariectomized controls. Further, animals given 2MD, at doses of at least 2.5 ng/kg/day, had a noticeable increase in lean body weight and bone mineral content (BMC) relative to the sham-operated or the ovariectomized controls. Significantly, the animals given 10 ng/kg/day 2MD not only had a higher lean body weight and bone mineral weight than either the sham-controls or ovariectomized controls but also had lower body fat and total body weight than either the ovariectomized or sham-operated controls. When the effect of 2MD is considered with respect to the body weight measurements in either set of controls, FIG. 4 shows that 2MD not only inhibits the weight gain shown for the ovariectomized animals but increases lean body weight and increases the bone mineral content when compared to the sham-operated controls.

In contrast, while animals given 200 ng/kg/day calcitriol did have less body fat than did the ovariectomized controls, the calcitriol treated animals still had a noticeable increase in body fat compared to the sham-operated controls. Further, the calcitriol group also showed an increase in overall body weight only when compared to the sham-controls, with only a tendency for reduction in body weight compared to the ovariectomized controls. Significantly, 2MD had a more positive effect on the increase in both lean body component and bone mineral component than did calcitriol, a recognized treatment for metabolic bone disease, when the calcitriol was given at 50 ng/kg/day. Calcitriol only exerted similar effects on the lean and bone mineral components when administered at doses of 200 ng/kg/day. It should be noted that animals given 2MD showed a trend for a decrease in the fat component, relative to the OVX-controls, starting at the 1 ng/kg/day dose such that the decrease in body fat relative to the OVX-controls was significant at 10 ng/kg/day. Further, the 10 ng/kg/day 2MD treated animals had less body fat than the basal body fat level of the sham-operated controls. It should be appreciated that, when normalized for humans, the rat dosage of 200 ng/kg/day is over twice the maximum recommended dosage for calcitriol therapy of 0.25–0.50 mcq recommended for humans. In humans, such dosages may lead to severe hypercalcemia which results in calcification of the vasculature, kidneys and other soft tissues and may be fatal. It should also be appreciated that, DEXA measurements erroneously indicating an increase in bone mineral content would result from soft tissue calcification. In contrast 2-alkyliden vitamin D compounds having a shortened side chain have low intestinal calcium transport activity, as discussed above, and generally, do not result in hypercalcemia.

When FIGS. 3 and 4 are considered together, the effects of 2MD are even more striking. Specifically, FIG. 3 illustrates the effect on the percentage of the body weight contributed by the fat component in response to various treatment regimes. With respect to the animals given 10 ng/kg/day 2MD, the resulting percent fat content of those animals is less than that of both the ovariectomized-controls and the sham-operated controls. When the individual body components are analyzed, the total body weight of the sham-control and 10 ng/kg/day 2MD groups are virtually the same. However, the decrease in body fat and increase in lean components of the 2MD group are enough to change the percent contribution of the body fat component, resulting in a noticeable difference between the sham-operated group, having a body fat content of 25%, and the group given 10 ng/kg/day 2MD, having a body fat content of only 20%. These results are even more impressive when considered next to that of calcitriol, which showed significance with respect to the ovariectomized controls only when the ovariectomized controls were given a potentially fatal dose of 200 ng/kg/day of calcitriol.

During the investigations disclosed herein, 2MD not only acted to decrease body fat but also acted to increased the lean body mass and bone mineral content (BMC) of the animals. Even at much higher doses, the native hormone, 1α,25-dihydroxyvitamin $D_3$ (i.e., calcitriol) did not act to significantly reduce the total body weight. In various exemplary embodiments, the 2-carbon modified analogs of 1α,25-dihydroxyvitamin $D_3$ according to this invention are especially active in decreasing body fat and total body weight and in particular the 2-alkylidene-19-nor-(20S or R)-1α,25-dihydroxyvitamin $D_3$ derivatives Various exemplary embodiments of methods according to this invention include reducing body fat in an animal by administering an effective amount of a 2-alkylidene-19-nor-1α,25-dihydroxyvitamin $D_3$ derivative. In various exemplary embodiments of methods according to this invention, the vitamin $D_3$ derivative administered is 2-methylene-19-nor-1-α,25-dihydroxyvitamin $D_3$ derivative. In other exemplary embodiments of methods according to this invention, the vitamin $D_3$ derivative administered is 2-methylene-19-nor-1α,25-dihydroxyvitamin $D_3$ derivative, in either the 20(S) or 20(R) conformations or a racemic mixture of both.

Similarly, other exemplary embodiments of methods according to this invention include the administration of a vitamin $D_3$ derivative that inhibits an increase in body fat in an animal that is prone to, or at risk of, an increased body fat composition by administering an effective amount of a 2-alkylidene-19-nor-1-α,25-dihydroxyvitamin $D_3$ derivative. In various other exemplary embodiments of methods according to this invention, the vitamin $D_3$ derivative is 2-methylene-19-nor-1α,25-dihydroxyvitamin $D_3$. In various exemplary embodiments, the 2-methylene-19-nor-1α,25-dihydroxyvitamin $D_3$ derivative is in either the 20 (S) or 20(R) conformation or a racemic mixture of both.

In other various exemplary embodiments, the methods according to this invention include the administration of a vitamin $D_3$ derivative that ameliorates the symptoms of menopause by administering an effective amount of a 2-alkylidene-19-nor-1α,25-dihydroxyvitamin $D_3$ derivative. In various other exemplary embodiments the methods according to this invention include the use of a 2-methylene-19-nor-1α,25-dihydroxyvitamin $D_3$ derivative. In various exemplary embodiments the 2-methylene-19-nor-1α,25-dihydroxyvitamin $D_3$ derivative is in either the 20 (S) or 20(R) conformation or a racemic mixture of both.

In various exemplary embodiments of methods according to this invention, the selected vitamin D compound can be administered daily. In various exemplary embodiments, the dose range of the selected compound can be between 0.001 and 1,000 μg/day, depending on the specific activity of the particular vitamin D compound selected. It should be appreciated that the vitamin D compound can be administered in any effective way.

To treat an animal, the compounds according to this invention can be formulated as solutions in innocuous solvents, or as emulsions, suspensions or dispersions in suitable innocuous solvents or carriers, or as pills, tablets or capsules, containing solid carriers, according to conventional methods known in the art. For topical applications, the compounds according to this invention are advantageously formulated as creams or ointments or similar vehicles suitable for topical applications. Any such formulations may also contain other pharmaceutically acceptable and non-toxic excipients, such as stabilizers, anti-oxidants, binders, coloring agents or emulsifying or taste-modifying agents.

In various exemplary embodiments, the compounds used in the methods described and claimed herein may be formulated with sustained release agents, such that the drug is released over an extended period of time and may or may not be delayed release. Generally, it should be appreciated that sustained release dosage forms are formulated by dispersing a drug within a matrix of a gradually bioerodible (hydrolyzable) material, such as an insoluble plastic, a hydrophilic polymer, a hydrogel or a fatty compound, or by coating a solid, drug-containing dosage form with such a material. Insoluble plastic matrices may include, for example, polyvinyl chloride or polyethylene.

Hydrophilic polymers useful for providing a sustained release coating or matrix cellulosic polymers include, but are not limited to, cellulosic polymers, usable acrylic acid polymers and copolymers, vinyl polymers and copolymers, zein; and shellac, ammoniated shellac, shellac-acetyl alcohol, and shellac n-butyl stearate, such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylcellulose phthalate, cellulose hexahydrophthalate, cellulose acetate hexahydrophthalate, and carboxymethylcellulose sodium. Usable acrylic acid polymers and copolymers, which can be formed from acrylic acid, include, for example, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate, with a terpolymer of ethyl acrylate, methyl methacrylate and trimethylammonioethyl methacrylate chloride (sold under the tradename Eudragit RS). Usable vinyl polymers and copolymers include, for example, polyvinyl pyrrolidone, polyvinyl acetate, polyvinylacetate phthalate, vinylacetate crotonic acid copolymer, and ethylene-vinyl acetate copolymers. Usable cellulosic polymers include, for example zein; and shellac, ammoniated shellac, shellac-acetyl alcohol, and shellac n-butyl stearate. Fatty compounds usable as a sustained release matrix material include, but are not limited to, waxes (e.g., carnauba wax) and glyccryl tristearate. However, it should be appreciated that the sustained release formulations for use with the disclosed vitamin D analogs are not limited to those described above and may include formulations currently known or yet to be discovered.

In variously exemplary embodiments of the methods according to this invention, the vitamin D analogs can be advantageously administered by injection, or by intravenous infusion of suitable sterile solutions, or in the form of oral doses via the alimentary canal, by inhalation via nasal dispersions or topically in the form of ointments, lotions, in suitable transdermal patches or in therapeutic implants.

In variously exemplary embodiments of the methods according to this invention, the vitamin D formulations may comprise an active ingredient in association with a pharmaceutically acceptable carrier for that active ingredient, and, optionally, other therapeutic ingredients. The carrier must be "acceptable" in the sense of being compatible with the other ingredients of the formulation and not deleterious to the animal receiving the formulation. Formulations of the vitamin D analogs usable with various exemplary embodiments of the methods according to this invention that are suitable for oral administration may be in the form of discrete units, such as capsules, sachets, tablets or lozenges, each containing a predetermined amount of the active ingredient; in the form of a powder or granules; in the form of a solution or a suspension in an aqueous or non-aqueous liquid; or in the form of an oil-in-water emulsion or a water-in-oil emulsion.

In various exemplary embodiments, formulations usable to therapeutically administer the vitamin D analogs usable with various exemplary embodiments of the methods according to this invention may be administered in the form of a therapeutic hydrogel implant. In such embodiments, the vitamin D analogs usable with various exemplary embodiments of the methods according to this invention may be contained within a biocompatible hydrogel, where the hydrogel may be in the form of an implantable capsule or prosthesis. Such hydrogels are described in, for example, U.S. Pat. Nos. 6,310,105 and 6,228,393, each incorporated herein by reference in its entirety.

In various exemplary embodiments, formulations usable to rectally administer the vitamin D analogs usable with various exemplary embodiments of the methods according to this invention may be in the form of a suppository incorporating the active ingredient and carrier such as, but not limited to, cocoa butter, a biocompatible hydrogel or in the form of an enema. Formulations suitably usable to parenterally administer the vitamin D analogs usable with various exemplary embodiments of the methods according to this invention conveniently comprise a sterile oily or aqueous preparation of the active ingredient, which is preferably isotonic with the blood of the recipient. Formulations suitably usable to topically administer the vitamin D analogs usable with various exemplary embodiments of the methods according to this invention include liquid or semi-liquid preparations, such as liniments, lotions, applicants, oil-in-water or water-in-oil emulsions such as creams, ointments or pastes; or solutions or suspensions such as drops; or as sprays.

The formulations may conveniently be presented in dosage unit form and may be prepared by any of the methods well known in the art of pharmacy. The term "dosage unit" means a unitary, i.e., single, dose, which is capable of being administered to a patient as a physically and chemically stable unit dose comprising either the active ingredient as such or a mixture of it with solid or liquid pharmaceutical diluents or carriers.

Various exemplary embodiments of methods according to this invention are described in the following illustrative examples: In these examples, specific products identified by Arabic numerals (e.g., 1, 2, 3, etc.) refer to the specific structures so identified in the following description and in SCHEME I and SCHEME II shown immediately preceding the claims.

The preparation of 1α-hydroxy-2-methylene-19-nor-vitamin D compounds having the basic structure I can be accomplished by a common general method, i.e. the condensation of a bicyclic Windaus-Grundmann type ketone II with the allylic phosphine oxide III:

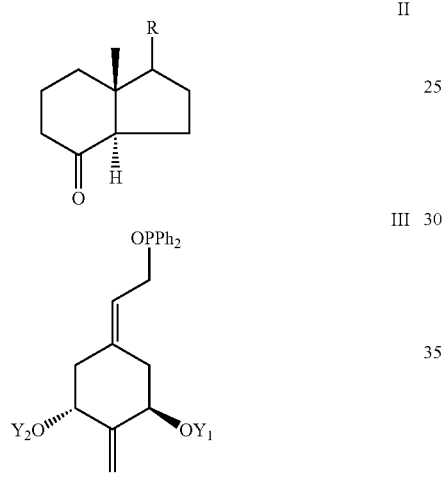

In the structures II and III, groups $Y^1$ and $Y^2$ and R represent those groups defined above. In various exemplary embodiments, $Y^1$ and $Y^2$ are hydroxy-protecting groups. However, it should be understood that any functionalities in R that might be sensitive, or that interfere with the condensation reaction, can be suitably protected, as is well-known in the art. The process shown above represents an application of the convergent synthesis concept, which has been applied effectively when preparing of vitamin D compounds, as discussed in, for example, Lythgoe et al., J. Chem. Soc. Perkin Trans. I, 590 (1978); Lythgoe, Chem. Soc. Rev. 9, 449 (1980); Toh et al., J. Org. Chem. 48, 1414 (1983); Baggiolini et al., J. Org. Chem. 51, 3098 (1986); Sardina et al., J. Org. Chem. 51, 1264 (1986); Mascarenas et al., J. Org. Chem. 51, 1269 (1986); each of which is incorporated herein by reference in its entirety and the previously-incorporated 191 and 713 patents.

Hydrindanones of the general structure II are known, or can be prepared by known methods. Specific important examples of such known bicyclic ketones are the structures with the side chains (a), (b), (c) and (d) described above, such as, for example, 25-hydroxy Grundmann's ketone (k), as disclosed in Baggiolini et al., J. Org. Chem, 51, 3098 (1986), Grundmann's ketone (l), as disclosed in Inhoffen et al., Chem. Ber. 90, 664 (1957), 25-hydroxy Windaus ketone (m), as disclosed in Baggiolini et al., J. Org. Chem., 51, 3098 (1986), and Windaus ketone (n), as disclosed in Windaus et al., Ann., 524, 297 (1936):

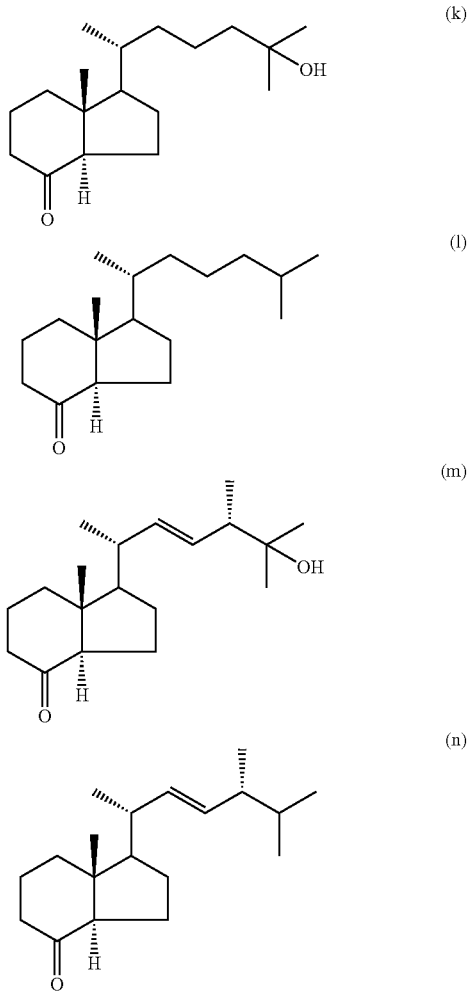

To prepare the required phosphine oxides of general structure III, a new synthetic route has been developed starting from methyl quinicate derivative 1, easily obtained from commercial (1R,3R,4S,5R)-(−)-quinic acid as described in Perlman et al, Tetrahedron Lett. 32, 7663 (1991), incorporated herein by reference in its entirety, and the previously incorporated 191 patent. The overall process of transforming of the starting methyl ester 1 into the desired A-ring synthons is summarized in SCHEME I. Thus, the secondary 4-hydroxyl group of 1 was oxidized with $RuO_4$, which is a catalytic method with $RuCl_3$ and $NaIO_4$ as co-oxidants. Using such a strong oxidant is desirable to effectively oxidize this very hindered hydroxyl. Other, more commonly used oxidants can also be applied, such as, for example, pyridinium dichromate. However, although the reactions usually take much longer time to complete. The second step of the synthesis comprises the Wittig reaction of the sterically hindered 4-keto compound 2 with ylide prepared from methyltriphenylphosphonium bromide and n-butyllithium. Other bases can be also used for the generation of the reactive methylenephosphorane, like t-BuOK, $NaNH_2$, NaH, K/HMPT, $NaN(TMS)_2$, etc.

For preparing of the 4-methylene compound 3, some described modifications of the Wittig process can be used, e.g. reaction of 2 with activated methylenetriphenylphosphorane, as disclosed in Corey et al., Tetrahedron Lett. 26, 555 (1985). Alternatively, other methods widely used for methylenation of unreactive ketones can be applied, e.g. Wittig-Horner reaction with the PO-ylid obtained from methyldiphenylphosphine oxide upon protonation with n-butyllithium, as disclosed in Schosse et al., Chimia 30, 197 (1976), or reaction of ketone with sodium methylsulfinate, as disclosed in Greenwald et al., J. Org. Chem. 28, 1128 (1963) and potassium methylsulfinate, as disclosed in Greene et al., Tetrahedron Lett. 17, 3755 (1976).

Reducing of the ester 3 with lithium aluminum hydride or other suitable reducing agent (e.g. DIBALH) provided the diol 4, which was subsequently oxidized by sodium periodate to the cyclohexanone derivative 5. The next step of the process comprises the Peterson reaction of the ketone 5 with methyl(trimethylsilyl)acetate. The resulting allylic ester 6 was treated with diisobutylaluminum hydride and the formed allylic alcohol 7 was in turn transformed to the desired A-ring phosphine oxide 8. Conversion of 7 to 8 involved 3 steps, namely, in situ tosylation with n-butyllithium and p-toluenesulfonyl chloride, followed by reaction with diphenylphosphine lithium salt and oxidation with hydrogen peroxide.

Several 2-methylene-19-nor-vitamin D compounds may be synthesized using the A-ring synthon 8 and the appropriate Windaus-Grundmann ketone having the desired side chain structure. Thus, for example, Wittig-Horner coupling of the lithium phosphinoxy carbanion generated from 8 and n-butyllithium with the protected 25-hydroxy Grundmann's ketone 9 prepared according to published procedure, as disclosed in Sicinski et al, J. Med. Chem. 37, 3730 (1994), gave the expected protected vitamin compound 10. This, after deprotection with AG 50W-X4 cation exchange resin afforded (20R) 1α,25-dihydroxy-2-methylene-19-nor-vitamin $D_3$ (11).

One interesting modification in the vitamin D side chain is C-20 epimerization. The coupling of the phosphine oxide 8 with protected (20S)-25-hydroxy Grundmann's ketone 13 (SCHEME II) provided 19-nor-vitamin 14 which after hydrolysis of the hydroxy-protecting groups gave (20S)-1α, 25-dihydroxy-2-methylene-19-nor-vitamin $D_3$ (15).

As noted above, other 19-nor-vitamin D analogs may be synthesized by the method disclosed herein. For example, 2-methylene-19-nor-1α-hydroxyvitamin $D_3$ can be obtained by providing the Grundmann's ketone (I).

Various exemplary embodiments of compounds obtained as generally described above and methods according to this invention, will be understood more readily by reference to the following examples, which are provided by way of illustration and are not intended to be limiting of the invention in any fashion.

EXAMPLES

Chemistry. Ultraviolet (UV) absorption spectra were recorded with a Hitachi Model 60-100 UV-vis spectrometer in the solvent noted. $^1$H nuclear magnetic resonance (NMR) spectra were recorded at 500 MHz with a Bruker AM-500 FT spectrometer in deuteriochloroform. Chemical shifts, (δ) are reported downfield from internal $Me_4Si$ (δ 0.00). Mass spectra were recorded at 70 eV on a Kratos DS-50 TC instrument equipped with a Kratos MS-55 data system. Samples were introduced into the ion source maintained at 120–250° C. via a direct insertion probe. High-performance liquid chromatography (HPLC) was performed on a Waters Associates liquid chromatograph equipped with a Model 6000A solvent delivery system, a Model 6 UK Universal injector, a Model 486 tunable absorbance detector, and a differential R 401 refractometer. Microanalyses of crystalline compounds were within ±0.4% of the theoretical values. THF was freshly distilled before use from sodium benzophenone ketyl under argon.

Example 1

PREPARATION OF 1α,25-DIHYDROXY-2-METHYLENE-19-NOR-VITAMIN $D_3$

Referring first to SCHEME I the starting methyl quinicate derivative 1 was obtained from commercial (−)-quinic acid as described previously in Perlman et al., Tetrahedron Lett. 32, 7663 (1991) and the previously incorporated 191 patent. 1: mp. 82°–82.5° C. (from hexane), $^1$H NMR ($CDCl_3$) δ 0.098, 0.110, 0.142, and 0.159 (each 3H, each s, 4×$SiCH_3$), 0.896 and 0.911 (9H and 9H, each s, 2×Si-t-Bu), 1.820 (1H, dd, J=13.1, 10.3 Hz), 2.02 (1H, ddd, J=14.3, 4.3, 2.4 Hz), 2.09 (1H, dd, J=14.3, 2.8 Hz), 2.19 (1H, ddd, J=13.1, 4.4, 2.4 Hz), 2.31 (1H, d, J=2.8 Hz, OH), 3.42 (1H, m; after $D_2O$ dd, J=8.6, 2.6 Hz), 3.77 (3H, s), 4.12 (1H, m), 4.37 (1H, m), 4.53 (1H, br s, OH).

(a) Oxidation of 4-hydroxy group in methyl quinicate derivative 1 to (3R,5R)-3,5-Bis[(tert-butyldimethylsilyl) oxy]-1-hydroxy-4-oxocyclohexanecarboxylic Acid Methyl Ester (2).

To a stirred mixture of ruthenium(III) chloride hydrate (434 mg, 2.1 mmol) and sodium periodate (10.8 g, 50.6 mmol) in water (42 ml) was added a solution of methyl quinicate 1 (6.09 g, 14 mmol) in $CCl_4/CH_3$ CN (1:1, 64 ml). Vigorous stirring was continued for 8 h. A few drops of 2-propanol were added, the mixture was poured into water and extracted with chloroform. The organic extracts were combined, washed with water, dried ($MgSO_4$) and evaporated to give a dark oily residue (ca. 5 g), which was purified by flash chromatography. Elution with hexane/ethyl acetate (8:2) gave pure, oily 4-ketone 2 (3.4 g, 56%): $^1$H NMR ($CDCl_3$) δ 0.054, 0.091, 0.127, and 0.132 (each 3H, each s, 4×$SiCH_3$), 0.908 and 0.913 (9H and 9H, each s, 2×Si-t-Bu), 2.22 (1H, dd, J=13.2, 11.7 Hz), 2.28 (1H, ~dt, J=14.9, 3.6 Hz), 2.37 (1H, dd, J=14.9, 3.2 Hz), 2.55 (1H, ddd, J=13.2, 6.4, 3.4 Hz), 3.79 (3H, s), 4.41 (1H, t, J~3.5 Hz), 4.64 (1H, s, OH), 5.04 (1H, dd, J=11.7, 6.4 Hz); MS m/z (relative intensity) no M+, 375 (M+-t-Bu, 32), 357 (M+-t-Bu-$H_2O$, 47), 243 (31), 225 (57), 73 (100).

(b) Wittig reaction of the 4-ketone 2 to (3R,5R)-3,5-Bis [(tert-butyldimethylsilyl)oxy]-1-hydroxy-4-methylenecyclohex-anecarboxylic Acid Methyl Ester (3).

To the methyltriphenylphoshonium bromide (2.813 g, 7.88 mmol) in anhydrous THF (32 ml) at 0° C. was added dropwise n-BuLi (2.5M in hexanes, 6.0 ml, 15 mmol) under argon with stirring. Another portion of $MePh_3$ P+Br−(2.813 g, 7.88 mmol) was then added and the solution was stirred at 0° C. for 10 min at room temperature for 40 min. The orange-red mixture was again cooled to 0° C. and a solution of 4-ketone 2 (1.558 g, 3.6 mmol) in anhydrous THF (16+2 ml) was siphoned to reaction flask during 20 min. The reaction mixture was stirred at 0° C. for 1 h and at room temperature for 3 h. The mixture was then carefully poured into brine containing 1% HCl and extracted with ethyl acetate and benzene. The combined organic extracts were washed with diluted $NaHCO_3$ and brine, dried ($MgSO_4$) and evaporated to give an orange oily residue (ca. 2.6 g), which was purified by flash chromatography. Elution with hexane/ ethyl acetate (9:1) gave pure 4-methylene compound 3 as a colorless oil (368 mg, 24%): $^1$H NMR (CDCl$_3$) δ 0.078, 0.083, 0.092, and 0.115 (each 3H, each s, 4×SiCH$_3$), 0.889 and 0.920 (9H and 9H, each s, 2×Si-t-Bu), 1.811 (1H, dd, J=12.6, 11.2 Hz), 2.10 (2H, m), 2.31 (1H, dd, J=12.6, 5.1 Hz), 3.76 (3H, s), 4.69 (1H, t, J=3.1 Hz), 4.78 (1H, m), 4.96 (2H, m; after D$_2$O 1H, br s), 5.17 (1H, t, J=1.9 Hz); MS m/z (relative intensity) no M+, 373 (M+-t-Bu, 57), 355 (M+-t-Bu-H$_2$O, 13), 341 (19), 313 (25), 241 (33), 223 (37), 209 (56), 73 (100).

(c) Reduction of ester group in the 4-methylene compound 3 to [(3R,5R)-3,5-Bis[(tert-butyldimethylsilyl)oxy]-1-hydroxy-4-methylenecyclohexyl]methanol (4).

(i) To a stirred solution of the ester 3 (90 mg, 0.21 mmol) in anhydrous THF (8 ml) lithium aluminum hydride (60 mg, 1.6 mmol) was added at 0° C. under argon. The cooling bath was removed after 1 h and the stirring was continued at 6° C. for 12 h and at room temperature for 6 h. The excess of the reagent was decomposed with saturated aqueous Na$_2$SO$_4$, and the mixture was extracted with ethyl acetate and ether, dried (MgSO$_4$) and evaporated. Flash chromatography of the residue with hexane/ethyl acetate (9:1) afforded unreacted substrate (12 mg) and a pure, crystalline diol 4 (35 mg, 48% based on recovered ester 3: $^1$H NMR (CDCl$_3$+D$_2$O) δ 0.079, 0.091, 0.100, and 0.121 (each 3H, each s, 4×SiCH$_3$), 0.895 and 0.927 (9H and 9H, each s, 2×Si-t-Bu), 1.339 (1H, t, J~12 Hz), 1.510 (1H, dd, J=14.3, 2.7 Hz), 2.10 (2H, m), 3.29 and 3.40 (1H and 1H, each d, J=11.0 Hz), 4.66 (1H, t, J~2.8 Hz), 4.78 (1H, m), 4.92 (1H, t, J=1.7 Hz), 5.13 (1H, t, J=2.0 Hz); MS m/z (relative intensity) no M+, 345 (M+-t-Bu, 8), 327 (M+-t-Bu-H$_2$O, 22), 213 (28), 195 (11), 73 (100).

(ii) Diisobutylaluminum hydride (1.5M in toluene, 2.0 ml, 3 mmol) was added to a solution of the ester 3 (215 mg, 0.5 mmol) in anhydrous ether (3 ml) at −78° C. under argon. The mixture was stirred at −78° C. for 3 h and at −24° C. for 1.5 h, diluted with ether (10 ml) and quenched by the slow addition of 2N potassium sodium tartrate. The solution was warmed to room temperature and stirred for 15 min, then poured into brine and extracted with ethyl acetate and ether. The organic extracts were combined, washed with diluted (ca. 1%) HCl, and brine, dried (MgSO$_4$) and evaporated. The crystalline residue was purified by flash chromatography. Elution with hexane/ethyl acetate (9:1) gave crystalline diol 4 (43 mg, 24%).

(d) Cleavage of the vicinal diol 4 to (3R,5R)-3,5-Bis[(tert-butyldimethylsilyl)oxy]-4-methylenecyclohexanone (5).

Sodium periodate saturated water (2.2 ml) was added to a solution of the diol 4 (146 mg, 0.36 mmol) in methanol (9 ml) at 0° C. The solution was stirred at 0° C. for 1 h, poured into brine and extracted with ether and benzene. The organic extracts were combined, washed with brine, dried (MgSO$_4$) and evaporated. An oily residue was dissolved in hexane (1 ml) and applied on a silica Sep-Pak cartridge. Pure 4-methylenecyclohexanone derivative 5 (110 mg, 82%) was eluted with hexane/ethyl acetate (95:5) as a colorless oil: $^1$H NMR (CDCl$_3$) δ 0.050 and 0.069 (6H and 6H, each s, 4×SiCH$_3$), 0.881 (18H, s, 2×Si-t-Bu), 2.45 (2H, ddd, J=14.2, 6.9, 1.4 Hz), 2.64 (2H, ddd, J=14.2, 4.6, 1.4 Hz), 4.69 (2H, dd, J=6.9, 4.6 Hz), 5.16 (2H, s); MS m/z (relative intensity) no M+, 355 (M+-Me, 3), 313 (M+-t-Bu, 100), 73 (76).

(e) Preparation of the allylic ester 6 [(3'R,5'R)-3',5'-Bis[(tert-butyldimethylsilyl)oxy]-4'-methylenecyclohexylidene]acetic Acid Methyl Ester from ketone 5.

To a solution of diisopropylamine (37 µl, 0.28 mmol) in anhydrous THF (200 µL) was added n-BuLi (2.5M in hexanes, 113 µL, 0.28 mmol) under argon at −78° C. with stirring, and methyl(trimethylsilyl)acetate (46 µL, 0.28 mmol) was then added. After 15 min, the keto compound 5 (49 mg, 0.132 mmol) in anhydrous THF (200+80 µl) was added dropwise. The solution was stirred at −78° C. for 2 h and the reaction mixture was quenched with saturated NH$_4$Cl, poured into brine and extracted with ether and benzene. The combined organic extracts were washed with brine, dried (MgSO$_4$) and evaporated. The residue was dissolved in hexane (1 ml) and applied on a silica Sep-Pak cartridge. Elution with hexane and hexane/ethyl acetate (98:2) gave a pure allylic ester 6 (50 mg, 89%) as a colorless oil: $^1$H NMR (CDCl$_3$) δ 0.039, 0.064, and 0.076 (6H, 3H, and 3H, each s, 4×SiCH$_3$), 0.864 and 0.884 (9H and 9H, each s, 2×Si-t-Bu), 2.26 (1H, dd, J=12.8, 7.4 Hz), 2.47 (1H, dd, J=12.8, 4.2 Hz), 2.98 (1H, dd, J=13.3, 4.0 Hz), 3.06 (1H, dd, J=13.3, 6.6 Hz), 3.69 (3H, s), 4.48 (2H, m), 4.99 (2H, s), 5.74 (1H, s); MS m/z (relative intensity) 426 (M+, 2), 411 (M+-Me, 4), 369 (M+-t-Bu, 100), 263 (69).

(f) Reduction of the allylic ester 6 to 2-[(3'R,5'R)-3',5'-Bis[(tert-butyldimethylsilyl)oxy]-4'-methylenecyclohexylidene]ethanol (7).

Diisobutylaluminum hydride (1.5M in toluene, 1.6 ml, 2.4 mmol) was slowly added to a stirred solution of the allylic ester 6 (143 mg, 0.33 mmol) in toluene/methylene chloride (2:1, 5.7 ml) at −78° C. under argon. Stirring was continued at −78° C. for 1 h and at −46° C. (cyclohexanone/dry ice bath) for 25 min. The mixture was quenched by the slow addition of potassium sodium tartrate (2N, 3 ml), aqueous HCl (2N, 3 ml) and H$_2$O (12 ml), and then diluted with methylene chloride (12 ml) and extracted with ether and benzene. The organic extracts were combined, washed with diluted (ca. 1%) HCl, and brine, dried (MgSO$_4$) and evaporated. The residue was purified by flash chromatography. Elution with hexane/ethyl acetate (9:1) gave crystalline allylic alcohol 7 (130 mg, 97%): $^1$H NMR (CDCl$_3$) δ 0.038, 0.050, and 0.075 (3H, 3H, and 6H, each s, 4×SiCH$_3$), 0.876 and 0.904 (9H and 9H, each s, 2×Si-t-Bu), 2.12 (1H, dd, J=12.3, 8.8 Hz), 2.23 (1H, dd, J=13.3, 2.7 Hz), 2.45 (1H, dd, J=12.3, 4.8 Hz), 2.51 (1H, dd, J=13.3, 5.4 Hz), 4.04 (1H, m; after D$_2$O dd, J=12.0, 7.0 Hz), 4.17 (1H, m; after D$_2$O dd, J=12.0, 7.4 Hz), 4.38 (1H, m), 4.49 (1H, m), 4.95 (1H, br s), 5.05 (1H, t, J=1.7 Hz), 5.69 (1H, ~t, J=7.2 Hz); MS m/z (relative intensity) 398 (M+, 2), 383 (M+-Me, 2), 365 (M+-Me-H$_2$O, 4), 341 (M+-t-Bu, 78), 323 (M+-t-Bu-H$_2$O, 10), 73 (100).

(g) Conversion of the allylic alcohol 7 to phosphine oxide 8 [2-[(3'R,5'R)-3',5'-Bis[(tert-butyldimethylsilyl)oxy]-4'-methylenecyclohexylidene]ethyl]diphenylphosphine Oxide (8).

To the allylic alcohol (7) (105 mg, 0.263 mmol) in anhydrous THF (2.4 ml) was added n-BuLi (2.5M in hexanes, 105 µl, 0.263 mmol) under argon at 0° C. Freshly recrystallized tosyl chloride (50.4 mg, 0.264 mmol) was dissolved in anhydrous THF (480 µl) and added to the allylic alcohol-BuLi solution. The mixture was stirred at 0° C. for 5 min and set aside at 0° C. In another dry flask with air replaced by argon, n-BuLi (2.5M in hexanes, 210 µl, 0.525 mmol) was added to Ph$_2$PH (93 µl, 0.534 mmol) in anhydrous THF (750 µl) at 0° C. with stirring. The red solution was siphoned under argon pressure to the tosylate solution of until the orange color persisted (ca. ½ of the solution was added). The resulting mixture was stirred an additional 30 min at 0° C., and quenched by addition of H$_2$O (30 µl). Solvents were evaporated under reduced pressure and the residue was redissolved in methylene chloride (2.4 ml) and stirred with 10% H$_2$O$_2$ at 0° C. for 1 h. The organic layer was separated, washed with cold aqueous sodium sulfite and H$_2$O, dried (MgSO$_4$) and evaporated. The residue was subjected to flash chromatography. Elution with benzene/ethyl acetate (6:4) gave semicrystalline phosphine oxide (8) (134 mg, 87%): $^1$H NMR (CDCl$_3$) δ 0.002, 0.011, and 0.019 (3H, 3H, and 6H, each s, 4×SiCH$_3$), 0.855 and 0.860 (9H and 9H, each s, 2×Si-t-Bu), 2.0–2.1 (3H, br m), 2.34 (1H, m), 3.08 (1H, m), 3.19 (1H, m), 4.34 (2H, m), 4.90 and 4.94

(1H and 1H, each s,), 5.35 (1H, ~q, J=7.4 Hz), 7.46 (4H, m), 7.52 (2H, m), 7.72 (4H, m); MS m/z (relative intensity) no M+, 581 (M+−1, 1), 567 (M+-Me, 3), 525 (M+-t-Bu, 100), 450 (10), 393 (48).

(h) Wittig-Horner coupling of protected 25-hydroxy Grundmann's ketone (9) with the phosphine oxide (8) to yield vitamin $D_3$ derivative 10.

To a solution of phosphine oxide 8 (33.1 mg, 56.8 μmol) in anhydrous THF (450 μl) at 0° C. was slowly added n-BuLi (2.5M in hexanes, 23 μl, 57.5 μmol) under argon with stirring. The solution turned deep orange. The mixture was cooled to −78° C. and a precooled (−78° C.) solution of protected hydroxy ketone 9 (9.0 mg, 22.8 μmol), prepared according to published procedure, as disclosed in Sicinski et al., J. Med. Chem. 37, 3730 (1994), in anhydrous THF (200+100 μl) was slowly added. The mixture was stirred under argon at −78° C. for 1 h and at 0° C. for 18 h. Ethyl acetate was added, and the organic phase was washed with brine, dried ($MgSO_4$) and evaporated. The residue was dissolved in hexane and applied on a silica Sep-Pak cartridge, and washed with hexane/ethyl acetate (99:1, 20 ml) to give 19-nor-vitamin derivative 10 (13.5 mg, 78%). The Sep-Pak was then washed with hexane/ethyl acetate (96:4, 10 ml) to recover some unchanged C,D-ring ketone 9 (2 mg), and with ethyl acetate (10 ml) to recover diphenylphosphine oxide (20 mg). For analytical purpose a sample of protected vitamin 10 was further purified by HPLC (6.2 mm×25 cm Zorbax-Sil column, 4 mL/min) using hexane/ethyl acetate (99.9:0.1) solvent system. Pure compound 10 was eluted at $R_V$ 26 ml as a colorless oil: UV (in hexane) $\lambda_{max}$ 244, 253, 263 nm; $^1$H NMR ($CDCl_3$) δ 0.025, 0.049, 0.066, and 0.080 (each 3H, each s, 4×$SiCH_3$), 0.546 (3H, s, 18-$H_3$), 0.565 (6H, q, J=7.9 Hz, 3×$SiCH_2$), 0.864 and 0.896 (9H and 9H, each s, 2×Si-t-Bu), 0.931 (3H, d, J=6.0 Hz, 21-$H_3$), 0.947 (9H, t, J=7.9 Hz, 3×$SiCH_2CH_3$), 1.188 (6H, s, 26- and 27-$H_3$), 2.00 (2H, m), 2.18 (1H, dd, J=12.5, 8.5 Hz, 4β-H), 2.33 (1H, dd, J=13.1, 2.9 Hz, 10β-H), 2.46 (1H, dd, J=12.5, 4.5 Hz, 4α-H), 2.52 (1H, dd, J=13.1, 5.8 Hz, 10α-H), 2.82 (1H, br d, J=12 Hz, 9β-H), 4.43 (2H, m, 1β- and 3α-H), 4.92 and 4.97 (1H and 1H, each s, =$CH_2$), 5.84 and 6.22 (1H and 1H, each d, J=11.0 Hz, 7- and 6-H); MS m/z (relative intensity) 758 (M+, 17), 729 (M+-Et, 6), 701 (M+-t-Bu, 4), 626 (100), 494 (23), 366 (50), 73 (92

(i) Deprotection of vitamin derivative 10 to yield 1α,25-Dihydroxy-2-methylene-19-nor-vitamin $D_3$ (11).

Protected vitamin 10 (4.3 mg) was dissolved in benzene (150 μl) and the resin (AG 50W-X4, 60 mg; prewashed with methanol) in methanol (800 μl) was added. The mixture was stirred at room temperature under argon for 17 h, diluted with ethyl acetate/ether (1:1, 4 ml) and decanted. The resin was washed with ether (8 ml) and the combined organic phases washed with brine and saturated $NaHCO_3$, dried ($MgSO_4$) and evaporated. The residue was purified by HPLC (6.2 mm.times.25 cm Zorbax-Sil column, 4 mL/min) using hexane/2-propanol (9:1) solvent system. Analytically pure 2-methylene-19-nor-vitamin $D_3$ (11) (2.3 mg, 97%) was collected at $R_V$ 29 ml (1α,25-dihydroxyvitamin $D_3$ was eluted at $R_V$ 52 ml in the same system) as a white solid: UV (in EtOH) $\lambda_{max}$ 243.5, 252, 262.5 nm; $^1$H NMR ($CDCl_3$) δ 0.552 (3H, s, 18-$H_3$), 0.941 (3H, d, J=6.4 Hz, 21-$H_3$), 1.222 (6H, s, 26- and 27-$H_3$), 2.01 (2H, m), 2.27–2.36 (2H, m), 2.58 (1H, m), 2.80–2.88 (2H, m), 4.49 (2H, m, 1β- and 3α-H), 5.10 and 5.11 (1H and 1H, each s, =$CH_2$), 5.89 and 6.37 (1H and 1H, each d, J=11.3 Hz, 7- and 6-H); MS m/z (relative intensity) 416 (M+, 83), 398 (25), 384 (31), 380 (14), 351 (20), 313 (100).

Example 2

PREPARATION OF (20S)-1α,25-DIHYDROXY-2-METHYLENE-19-NOR-VITAMIN $D_3$

SCHEME II illustrates the preparation of protected (20S)-25-hydroxy Grundmann's ketone 13, and its coupling with phosphine oxide 8 (obtained as described in Example 1).

(a) Silylation of hydroxy ketone 12 to (20S)-25-[(Triethylsilyl)oxy]-des-A,B-cholestan-8-one (13).

A solution of ketone 12 (Tetrionics, Inc., Madison, Wis.); (56 mg, 0.2 mmol) and imidazole (65 mg, 0.95 mmol) in anhydrous DMF (1.2 ml) was treated with triethylsilyl chloride (95 μl, 0.56 mmol), and the mixture was stirred at room temperature under argon for 4 h. Ethyl acetate was added and water, and the organic layer was separated. The ethyl acetate layer was washed with water and brine, dried ($MgSO_4$) and evaporated. The residue was passed through a silica Sep-Pak cartridge in hexane/ethyl acetate (9:1), and after evaporation, purified by HPLC (9.4 mm×25 cm Zorbax-Sil column, 4 mL/min) using hexane/ethyl acetate (9:1) solvent system. Pure protected hydroxy ketone 13 (55 mg, 70%) was eluted at $R_V$ 35 ml as a colorless oil: $^1$H NMR ($CDCl_3$) δ 0.566 (6H, q, J=7.9 Hz, 3×$SiCH_2$), 0.638 (3H, s, 18-$H_3$), 0.859 (3H, d, J=6.0 Hz, 21-$H_3$), 0.947 (9H, t, J=7.9 Hz, 3×$SiCH_2CH_3$), 1.196 (6H, s, 26- and 27-$H_3$), 2.45 (1H, dd, J=11.4, 7.5 Hz, 14.alpha.-H).

(b) Wittig-Homer coupling of protected (20S)-25-hydroxy Grundmann's ketone 13 with the phosphine oxide 8 to yield protected vitamin $D_3$ derivative 14.

To a solution of phosphine oxide 8 (15.8 mg, 27.1 μmol) in anhydrous THF (200 μl) at 0° C. was slowly added n-BuLi (2.5M in hexanes, 11 μl, 27.5 μmol) under argon with stirring. The solution turned deep orange. The mixture was cooled to −78° C. and a precooled (−78° C.) solution of protected hydroxy ketone 13 (8.0 mg, 20.3 μmol) in anhydrous THF (100 μl) was slowly added. The mixture was stirred under argon at −78° C. for 1 h and at 0° C. for 18 h. Ethyl acetate was added, and the organic phase was washed with brine, dried ($MgSO_4$) and evaporated. The residue was dissolved in hexane and applied on a silica Sep-Pak cartridge, and washed with hexane/ethyl acetate (99.5:0.5, 20 ml) to give 19-nor-vitamin derivative 14 (7 mg, 45%) as a colorless oil. The Sep-Pak was then washed with hexane/ethyl acetate (96:4, 10 ml) to recover some unchanged C,D-ring ketone 13 (4 mg), and with ethyl acetate (10 ml) to recover diphenylphosphine oxide (9 mg). For analytical purposes a sample of protected vitamin 14 was further purified by HPLC (6.2 mm×25 cm Zorbax-Sil column, 4 mL/min) using hexane/ethyl acetate (99.9:0.1) solvent system. 14: UV (in hexane) $\lambda_{max}$ 244, 253.5, 263 nm; $^1$H NMR ($CDCl_3$) δ 0.026, 0.049, 0.066, and 0.080 (each 3H, each s, 4×$SiCH_3$), 0.541 (3H, s, 18-$H_3$), 0.564 (6H, q, J=7.9 Hz, 3×$SiCH_2$), 0.848 (3H, d, J=6.5 Hz, 21-$H_3$), 0.864 and 0.896 (9H and 9H, each s, 2×Si-t-Bu), 0.945 (9H, t, J=7.9 Hz, 3×$SiCH_2CH_3$), 1.188 (6H, s, 26- and 27-$H_3$), 2.15–2.35 (4H, br m), 2.43–2.53 (3H, br m), 2.82 (1H, br d, J=12.9 Hz, 9β-H), 4.42 (2H, m, 1β- and 3α-H), 4.92 and 4.97 (1H and 1H, each s, =$CH_2$), 5.84 and 6.22 (1H and 1H, each d, J=11.1 Hz, 7- and 6-H); MS m/z (relative intensity) 758 (M+, 33), 729 (M+-Et, 7), 701 (M+-t-Bu, 5), 626 (100), 494 (25), 366 (52), 75 (82), 73 (69

Deprotection of vitamin D3 derivative 14 to yield (20S)-1α,25-Dihydroxy-2-methylene-19-nor-vitamin $D_3$ (15)

Protected vitamin 14 (5.0 mg) was dissolved in benzene (160 μl) and the resin (AG 50W-X4, 70 mg; prewashed with methanol) in methanol (900 μl) was added. The mixture was stirred at room temperature under argon for 19 h, diluted with ethyl acetate/ether (1:1, 4 ml) and decanted. The resin was washed with ether (8 ml) and the combined organic phases washed with brine and saturated NaHCO$_3$, dried (MgSO$_4$) and evaporated. The residue was purified by HPLC (6.2 mm×25 cm Zorbax-Sil column, 4 mL/min) using hexane/2-propanol (9:1) solvent system. Analytically pure (20S)-1α,25-Dihydroxy-2-methylene-19-nor-vitamin D$_3$ (15) (2.6 mg, 95%) was collected at R$_V$ 28 ml [(20R)-analog was eluted at R$_V$ 29 ml and 1α,25-dihydroxyvitamin D$_3$ at R$_V$ 52 ml in the same system] as a white solid: UV (in EtOH) λ$_{max}$ 243.5, 252.5, 262.5 nm; $^1$H NMR (CDCl$_3$) δ 0.551 (3H, s, 18-H$_3$), 0.858 (3H, d, J=6.6 Hz, 21-H$_3$), 1.215 (6H, s, 26- and 27-H$_3$), 1.95–2.04 (2H, m), 2.27–2.35 (2H, m), 2.58 (1H, dd, J=13.3, 3.7 Hz), 2.80–2.87 (2H, m), 4.49 (2H, m, 1β- and 3α-H), 5.09 and 5.11 (1 H and 1H, each s, =CH$_2$), 5.89 and 6.36 (1H and 1H, each d, J=11.3 Hz, 7- and 6-H); MS m/z (relative intensity) 416 (M+, 100), 398 (26), 380 (13), 366 (21), 313 (31).

Example 3

EFFECT OF 2-METHYLENE-19-NOR-(20S)-1α, 25-DIHYDROXY-VITAMIN D$_3$ ON OVARIECTOMIZED RATS

FIG. 1 is a flow-chart illustrating the experimental design of the investigations described herein. Female Sprague Dawley rats (Taconic, German Town, N.Y.) were placed on a purified diet of 0.5% calcium and 0.4% phosphorus (AIN-76A Rodent Diet, prepared by Research Diet, Inc., New Brunswick, N.J.). At 4 months of age, a first subset (20) of the animals was sham-operated while a second subset (90) was ovariectomized. The time of ovariectomy is designated as week 0. Eight weeks after this surgery, the ovariectomized animals were divided into experimental groups receiving the following dosing regimen: 2MD, at doses of 0.5, 1.0, 2.5, 5.0 and 10 ng/kg/day; calcitriol (the active form of vitamin D), at doses of 50 ng/kg/day and 200 ng/kg/day; and human parathyroid hormone hPTH, at doses of 20 μg/kg/day. The 2MD and the calcitriol were administered orally in 100 μl of vegetable oil delivered to the back of the tongue by a throat tube, while the hPTH was administered sub-cutaneously.

Serum calcium was measured by tail bleeding at week 14 (6 weeks post-surgery), week 21 and week 24. At week 24, the animals were sacrificed and the following endpoint measurements were taken: whole body DEXA; bone markers: osteocalcin and deoxypyridinoline (DPD); peripheral quantitative computed tomography (pQCT) of the distal femoral metaphysis (DFM) and femoral shaft (FS); micro-computerized tomography (micro-CT) of the DFM; serum parathyroid hormone (PTH); histomorphometry of the proximal tibial metaphysis (PTM), lumbar vertebra 3 (LV3) and trabecular separation (TS); and bone strength of the DFM, FS and lumbar vertebra 5 (LV5).

FIG. 2 gives further details the experimental design shown in FIG. 1. At week 0, the animals underwent surgical treatment as explained above. The animals were allowed to recuperate for 8 weeks before the dosing regimen began (0 wk). At 24 weeks post-surgery the animals were sacrificed and endpoint measurements were taken as explained above.

FIG. 3 shows the change in percent body fat as a function of the dosing regimen. Ovariectomized controls show a significantly increased percent body fat compared with the sham-operated controls. Administering of 2MD had little to no effect on the percent body fat of the ovariectomized animals at the 0.5 and 1 ng/kg/day levels compared to the ovariectomized/vehicle control animals. However, there was a significant decrease in percent body fat of the experimental groups given 2MD at both 5 and 10 ng/kg/day compared to the ovariectomized control animals. In contrast, there was at most only a minor difference between the animals given 50 ng/kg/day of calcitriol or 20 hPTH μg/kg/day and the ovariectomized control animals. Animals given 200 ng/kg/day calcitriol did exhibit a significant decrease in percentage body fat similar to those animals dosed at 5 ng/kg/day 2MD.

The results illustrated in FIG. 3 show that 5 ng/kg/day 2MD has as great an effect on the reduction in body fat as calcitriol at 200 ng/kg/day. Those animals receiving 2MD at the 10 ng/kg day had a greater decrease in the fat component than did the group receiving 200 ng/kg/day calcitriol. Moreover, those animals receiving 2MD at the 10 ng/kg/day level also had a decrease in body fat relative to the sham-operated controls.

FIG. 4 is a histogram showing the results of the dosage protocol on the individual tissue components in percentage of the experimental groups described in FIGS. 1–3. FIG. 4 shows the contribution to the total body weight from each of the fat component, lean tissue component, and lean tissue plus bone mineral content component, as measured by the DEXA technique. These results indicate that ovariectomy results in an increase in total body weight for the experimental animals, with the majority of that increase resulting from an increase in the fat component of the animals, relative to the sham/vehicle control animals.

The experimental group given 5 ng/kg/day of 2MD had significantly less body fat than the ovariectomized-vehicle controls, while their total body weight was significantly increased over the sham/vehicle controls. Further, this group showed an increase in the lean component and the bone mineral content (BMC) component when compared to the sham-operated control animals. This result indicates that the increase in body weight, relative to the sham-control animals, increases the lean body weight component and the BMC component of the animals. The experimental animals dosed with 10 ng/kg/day of 2MD had a body fat component similar to the sham operated animals, a value that was significantly lower than the ovariectomized control animals. Further, those animals given 10 ng/kg/day of 2MD had an increased lean body weight and lean body weight plus bone mineral content, relative to the sham operated animals. These results show that 2MD, at doses of 10 ng/kg/day, inhibited an increase in fat that was expected of the ovariectomized control animals and also decreased the basal fat content relative to the sham-operated control animals. Further, the group of animals given 10 ng/kg/day 2MD had significantly reduced body weight compared to the ovariectomized control animals. The decreased body weight, resulting from decrease body fat, provided a sparing or restorative effect on the protein (lean body) and bone mineral components of the animals, as illustrated by the maintenance of pre-surgery weight resulting from decreased fat but increased lean and lean BMC weight.

The results described herein illustrate the effects of 2MD in reducing body fat composition. Without being held to any particular theory, the effect of 2MD on fat content is thought to be a result from an effect of 2MD on the maturation, differentiation and proliferation of adipocytes, see, for example, U.S. patent application Ser. No. 10/997,698 titled, "Vitamin D Analogs for Obesity Prevention and Treatment" filed Nov. 24, 2004, by Clagett-Dame et al. and incorporated herein by reference in its entirety. Various exemplary embodiments of methods according to this invention, as described herein, can be used for animals that are at risk for overweight or are already overweight. Similarly, various exemplary embodiments of methods according to this invention can be used to reduce body fat percent in animals that are obese or are at risk of becoming obese.

In addition, due to their ability to decrease body fat while promoting bone restoration and/or regeneration, various exemplary embodiments of methods according to this invention, as described herein, can be used to treat animals that are concurrently at risk for increased overweight or obesity and degenerative bone diseases, such as osteoporosis. Various exemplary embodiments of methods according to this invention, as described herein, include administering compounds in effective doses to ameliorate the effects of menopause.

As described herein, various exemplary embodiments of methods according to this invention can be used prophylactically to treat animals that are overweight with a risk of becoming obese or animals that are at risk of becoming overweight. In addition, various exemplary embodiments of methods according to this invention can be used prophylactically to promote a healthy body composition and to avoid the risks associated with overweight and/or obesity, such as cardiovascular disease cancers, urinary incontinence, diabetes and the like.

While this invention has been described in conjunction with the various exemplary embodiments outlined above, various alternatives, modifications, variations, improvements, and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments.

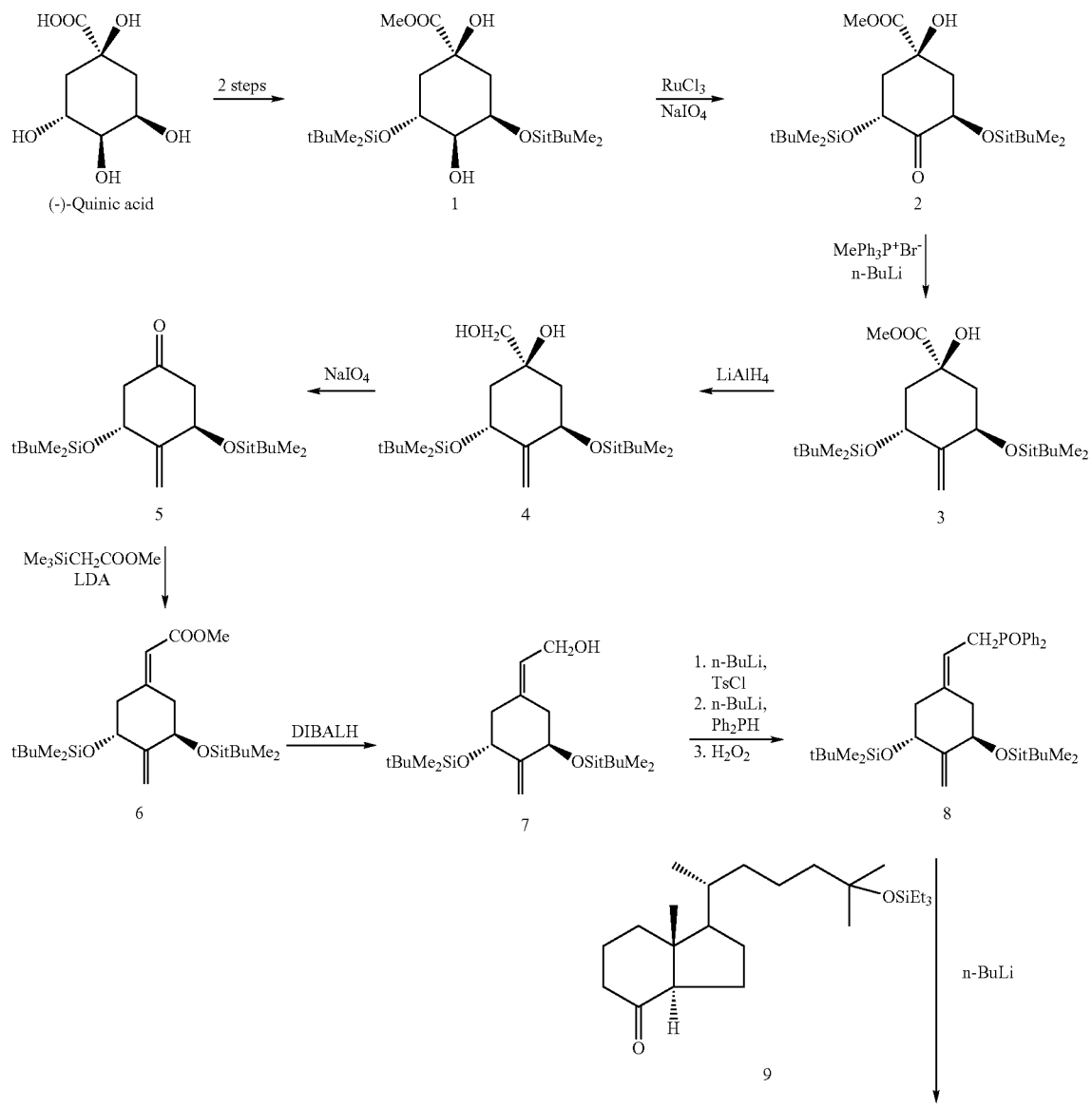

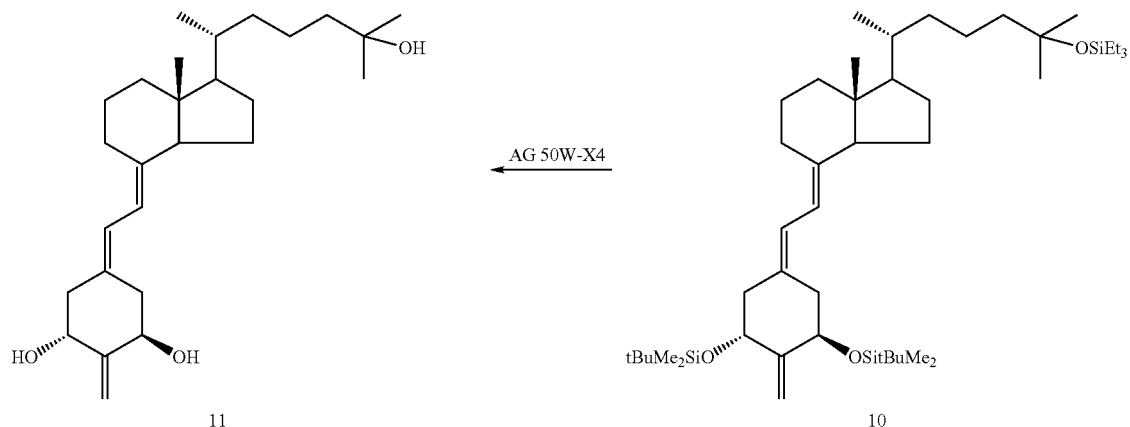
SCHEME II
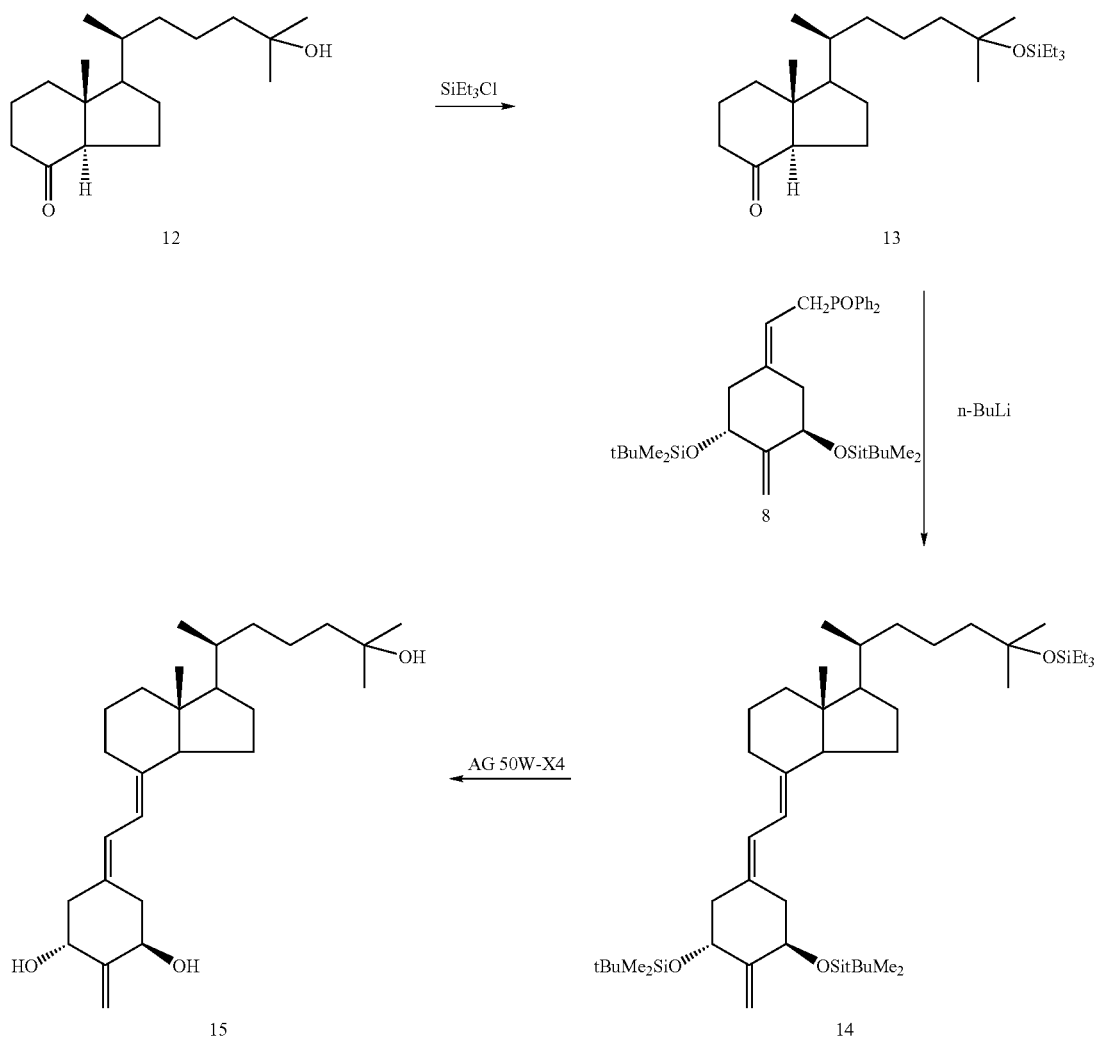

What is claimed is:

1. A method of treating obesity comprising administering to a patient in need thereof a therapeutically effective amount of a vitamin D compound comprising 2-methylene-19-nor-(20S) 1 α,25 dihydroxyvitamin $D_3$.

2. The method of claim 1, wherein administering to the patient comprises administering to a mammal.

3. The method of claim 1, wherein administering the vitamin D compound does not reduce the lean body component while reducing body fat of the patient.

4. The method of claim 1, wherein administering the vitamin D compound comprises administering the vitamin D compound orally, parenterally, transdermally, nasally, rectally, by timed release implant or by therapeutic implant.

5. The method of claim 1, wherein administering the vitamin D compound comprises administering the vitamin D compound combined with a pharmaceutically acceptable carrier.

6. The method of claim 1, wherein administering the vitamin D compound comprises administering the vitamin D compound at a dosage of from about 0.001 µg per day to 100 mg per day.

7. The method of claim 6, wherein administering the vitamin D compound comprises administering the vitamin D compound at a dosage range of from about 0.001 µg per day to 100.0 µg per day.

8. The method of claim 1, wherein administering the vitamin D compound comprises administering a vitamin D compound having a formula:

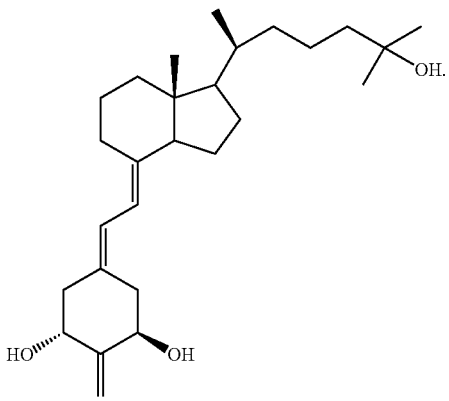

9. A method of decreasing the percent body fat of an animal comprising administering to a patient in need thereof a therapeutically effective amount of a vitamin D compound comprising 2-methylene-19-nor(20S) 1α,25 dihydroxyvitamin $D_3$ having the formula:

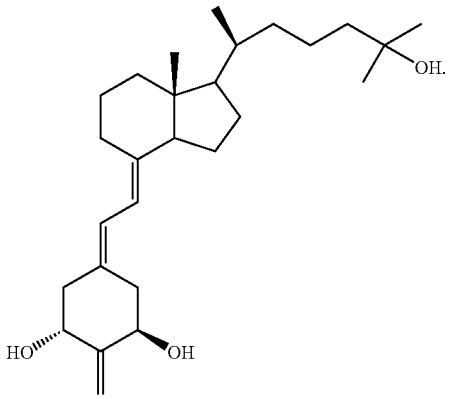

10. The method of claim 9, wherein administering to the patient comprises administering to a mammal.

11. The method of claim 9, wherein administering the vitamin D compound does not reduce the lean body component of the animal.

12. The method of claim 9, wherein administering the vitamin D compound comprises administering the vitamin D compound orally, parenterally, nasally, transdermally, rectally, by timed release implant or by therapeutic implant.

13. The method of claim 9, wherein administering the vitamin D compound comprises administering the vitamin D compound combined with a pharmaceutically acceptable carrier.

14. The method of claim 9, wherein administering the vitamin D compound comprises administering the vitamin D compound at a dosage of from about 0.001 µg per day to 100 mg day.

15. The method of claim 14, wherein administering the vitamin D compound comprises administering the vitamin D compound at a dosage range of from about 0.001 µg per day to 100.0 µg per day.

16. A method of inhibiting an increase in body weight comprising administering to a patient in need thereof a therapeutically effective amount of a vitamin D compound comprising 2-methylene-19-nor-(20S) 1α,25 dihydroxyvitamin $D_3$.

17. The method of claim 16, wherein administering to the patient is administering to a mammal.

18. The method of claim 16, wherein administering the vitamin D compound does not reduce the lean body component of the animal.

19. The method of claim 16, wherein administering the vitamin D compound comprises administering the vitamin D compound orally, parenterally, nasally, transdermally, rectally, by timed release implant or by therapeutic implant.

20. The method of claim 16, wherein administering the vitamin D compound comprises administering the vitamin D compound combined with a pharmaceutically acceptable carrier.

21. The method of claim 16, wherein administering the vitamin D compound comprises administering the vitamin D compound at a dosage of from about 0.001 µg per day to 100 mg day.

22. The method of claim 21, wherein administering the vitamin D compound comprises administering the vitamin D compound at a dosage range of from about 0.001 µg per day to 100.0 µg per day.

23. The method of claim 16, wherein administering the vitamin D compound comprises administering a vitamin D compound having a formula:

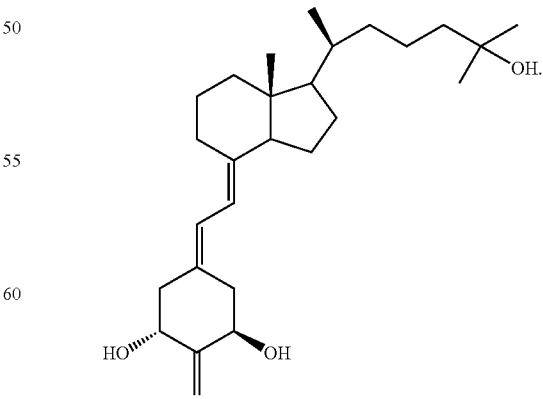

24. A method of treating the symptoms of menopause, wherein the symptoms of menopause include weight gain and osteoporosis comprising administering to a patient in need thereof a therapeutically effective amount of a vitamin D compound comprising 2-methylene-19-nor-(20S) 1α,25 dihydroxyvitamin $D_3$.

25. The method of claim 24, wherein administering to the patient comprises administering to a mammal.

26. The method of claim 24, wherein administering the vitamin D compound does not reduce the lean body component while reducing body fat of the patient.

27. The method of claim 24, wherein administering the vitamin D compound comprises administering the vitamin D compound orally, parenterally, transdermally, nasally, rectally, by timed release implant or by therapeutic implant.

28. The method of claim 24, wherein administering the vitamin D compound comprises administering the vitamin D compound combined with a pharmaceutically acceptable carrier.

29. The method of claim 24, wherein administering the vitamin D compound comprises administering the vitamin D compound at a dosage of from about 0.001 μg per day to 100 mg per day.

30. The method of claim 29, wherein administering the vitamin D compound comprises administering the vitamin D compound at a dosage range of from about 0.001 μg per day to 100.0 μg per day.

31. The method of claim 24, wherein administering the vitamin D compound comprises administering the vitamin D compound having a formula:

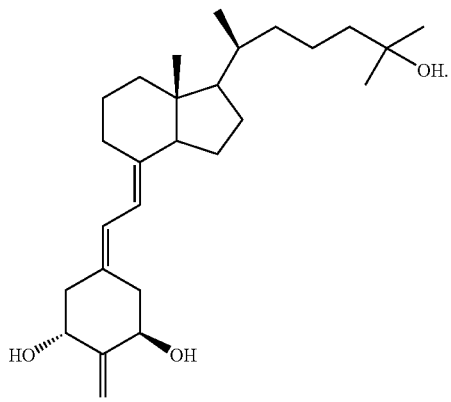

* * * * *